United States Patent
Klar et al.

(10) Patent No.: US 6,596,713 B1
(45) Date of Patent: *Jul. 22, 2003

(54) STEROID ESTERS AND AMIDES, PROCESS FOR THEIR PRODUCTION AND THEIR PHARMACEUTICAL USE

(75) Inventors: Ulrich Klar, Berlin (DE); Arwed Cleve, Berlin (DE); Guenter Neef, Berlin (DE); Eckhard Ottow, Berlin (DE); Klaus Stoekemann, Berlin (DE); Karl-Heinrich Fritzemeier, Berlin (DE)

(73) Assignee: Schering Aktiengesellschaft, Berlin (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/914,176

(22) Filed: Aug. 19, 1997

Related U.S. Application Data

(63) Continuation of application No. 08/527,512, filed on Sep. 14, 1995, now abandoned.

(30) Foreign Application Priority Data

Sep. 14, 1994 (DE) .......................................... 44 43 488

(51) Int. Cl.⁷ ........................ A61K 31/56; A61K 31/58; C07J 53/00
(52) U.S. Cl. ...................... 514/179; 514/176; 552/510; 540/47
(58) Field of Search ................................ 552/510, 540, 552/543, 546, 548, 552, 554, 555; 550/650; 514/182, 179, 176; 540/47

(56) References Cited

U.S. PATENT DOCUMENTS

| | | | |
|---|---|---|---|
| 4,477,445 A | 10/1984 | Philibert et al. | 424/239 |
| 4,540,686 A | 9/1985 | Philibert et al. | 514/179 |
| 4,609,651 A | 9/1986 | Rohde et al. | 514/179 |
| 4,780,461 A * | 10/1988 | Neef et al. | 514/179 |
| 4,814,327 A * | 3/1989 | Ottow et al. | 514/179 |
| 4,829,060 A * | 5/1989 | Ottow et al. | 514/179 |
| 4,871,724 A | 10/1989 | Groen et al. | 514/173 |
| 4,921,845 A | 5/1990 | de Jongh et al. | 514/172 |
| 5,064,822 A | 11/1991 | Philibert et al. | 514/172 |
| 5,095,129 A | 3/1992 | Ottow et al. | 552/510 |
| 5,173,483 A | 12/1992 | Grandadam | 514/178 |
| 5,182,381 A | 1/1993 | Philibert et al. | 540/4 |
| 5,244,886 A * | 9/1993 | Scholz et al. | 514/175 |
| 5,273,971 A * | 12/1993 | Scholz et al. | 514/176 |
| 5,276,023 A * | 1/1994 | Moguilewsky et al. | 514/179 |
| 5,446,036 A * | 8/1995 | Scholz et al. | 514/175 |
| 5,446,178 A | 8/1995 | Ottow et al. | 552/510 |

FOREIGN PATENT DOCUMENTS

| | | | |
|---|---|---|---|
| CA | 2019404 | 12/1990 | .............. C07J/1/00 |
| DE | 34 46 661 | 12/1984 | .............. C07J/41/00 |
| EP | 0 129 499 | 6/1984 | .............. C07J/41/00 |
| EP | 0 147 361 | 12/1984 | .............. C07J/41/00 |
| EP | 0 283 428 | 3/1988 | .............. C07J/53/00 |
| EP | 0 289 073 | 4/1988 | .............. C07J/41/00 |
| EP | 0 312 010 | 11/1988 | .............. C07J/41/00 |
| EP | 0 404 283 | 6/1990 | .............. C07J/43/00 |
| EP | 0 412 907 | 8/1990 | .............. C07J/41/00 |
| EP | 0 417 003 | 9/1990 | ......... A61K/31/565 |
| FR | 2 586 021 | 9/1985 | .............. C07J/1/00 |
| WO | WO83/03099 | 9/1983 | .............. C07J/1/00 |

OTHER PUBLICATIONS

*Steroids*, 13(3), Mar. 1969, pp 278–310.*

* cited by examiner

*Primary Examiner*—Barbara P. Badio
(74) *Attorney, Agent, or Firm*—Millen, White, Zelano & Branigan, P.C.

(57) ABSTRACT

New steroids and amides of formula I

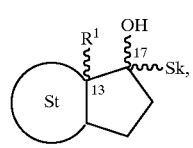

are described, in which the variables are defined by the description. Relative to the basic hydroxy compounds ("initial compounds"), the new compounds are distinguished by a considerably improved solubility and partially also by increased biological action and selectivity. The new compounds are suitable for the production of pharmaceutical agents.

21 Claims, No Drawings

STEROID ESTERS AND AMIDES, PROCESS FOR THEIR PRODUCTION AND THEIR PHARMACEUTICAL USE

The application is a continuation, of application Ser. No. 08/527,512, now abandoned filed Sep. 14, 1995.

The invention relates to steroid esters and amides, . . . as well as their use as adjuvants for pharmacological studies and as pharmaceutical substances.

The invention relates to steroid esters and amides of formula I

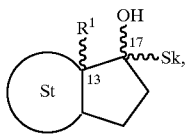

I in which
$R^1$ means a $C_1$–$C_3$ alkyl radical in α- or β-position,
Sk means —C≡C—$(CH_2)_r$—$R^2$, (E) or (Z)—CH=CH—$(CH_2)_r$—$R^2$, —$(CH_2)_2$—$(CH_2)_r$—$R^2$,
r means 1, 2 or 3,
$R^2$ means —O—$(X^i_1$—$X^i_2$—$X^i_3$— . . . —$X^i_p)$—$R^5$, —C(=O)—$(Y^i_1$—$Y^1_2$—$Y^i_3$— . . . —$Y^i_p)$—$OR^5$, —OC(=O)$R^3$, —NHC(=O)$R^3$,
$R^3$ means —L—$R^4$,
L means an n-membered, straight- or branched-chain alkylene group,
n, if St stands for an ABC-ring system of partial formula B, $R^1$ stands for a methyl group in α-position, Sk stands for a radical of formula —$(CH_2)_3$—O—C(=O)—L—$R^4$ and $R^4$ stands for a hydrogen atom, n means an integer from 11 to 20; if St stands for an ABC-ring system of partial formula B, $R^1$ stands for a $C_1$–$C_2$ alkyl radical in βposition, Sk stands for a radical of formula —CH=CH—$CH_2$—O—C(=O)—L—$R^4$ and $R^4$ stands for a hydrogen atom, n means an integer from 9 to 20; and in all other cases in which St stands for B, $R^2$ stands for —OC(=O)$R^3$ and $R^4$ stands for a hydrogen atom, n means an integer from 5 to 20, or if St stands for an ABC-ring system of partial formula A, Sk stands for a radical of formula (E) or (Z)—CH=CH—$(CH_2)_r$—O—C(=O)—L—$R^4$ and $R^4$ stands for a hydrogen atom, n means an integer from 5 to 20; if St stands for an ABC-ring system of partial formula A, Sk stands for a radical of formula —$(CH_2)_2$—$(CH_2)_r$—O—C(=O)—L—$R^4$ and $R^4$ stands for a hydrogen atom, n means an integer from 11 to 20 or if St stands for an ABC-ring system of partial formula C, $R^2$ stands for —OC(=O)$R^3$ and $R^4$ stands for a hydrogen atom, n means an integer from 5 to 20; and in all other cases, n means an integer from 2 to 20,
p means an integer from 1 to 6,
$R^4$ means hydrogen, —O—$(X^i_1$—$X^i_2$—$X^i_3$— . . . —$X^i_p)$—$R^5$, —C(=O)—$(Y^i_1$—$Y^1_2$—$Y^i_3$— . . . —$Y^i_p)$—$OR^5$, —$OR^5$, a $C_3$–$C_{10}$ cycloalkyl radical, —C(=O)$R^{5a}$,
$R^5$ means hydrogen, a $C_1$–$C_{10}$ alkyl radical,
$R^{5a}$ means hydrogen, a $C_1$–$C_{10}$ alkyl radical, a $C_1$–$C_{10}$ alkoxy radical,
$X^i_{1...p}$ are the same or different and mean —[—C(O)—W—NH—]—=X, and X as HO—X—H is an α-, β- or γ-amino acid that is linked on its C-terminal end, $Y^i_{1...p}$ are the same or different and mean —[—NH—W—C(O)—]—=Y, and Y as H—Y—OH is an α-, β- or γ-amino acid that is linked on its N-terminal end, St represents one of the steroidal ABC-ring systems of partial formula A, B or C

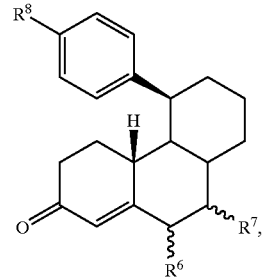

A

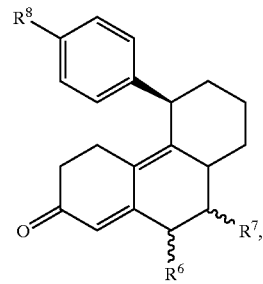

B

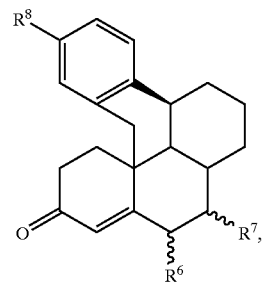

C $R^6$ means hydrogen, $C_1$–$C_4$ alkyl, halogen,
$R^7$ means hydrogen, $C_1$–$C_4$ alkyl, halogen, and further an additional bond can be contained between carbon atoms 6 and 7 of ring systems A, B and C,
$R^8$ means a group Z or an aryl radical optionally substituted several times by a group Z,
Z means hydrogen, halogen, —OH, —$NO_2$, —$N_3$, —CN, —$NR^{9a}R^{9b}$, —$NHSO_2R^9$, —$CO_2R^9$, $C_1$–$C_{10}$ alkyl, $C_1$–$C_{10}$ alkoxy, $C_1$–$C_{10}$ acyloxy, $C_1$–$C_{10}$ acyl,
$R^{9a,b}$ are the same or different and have one of the meanings mentioned under $R^9$,
$R^9$ means hydrogen or $C_1$–$C_{10}$ alkyl and, if $R^9$ is hydrogen, further their physiologically compatible salts with bases (Z=—$CO_2H$) or acids (Z=—$NR^{9a}R^{9b}$)

The wavy lines that start from carbon atom 17 on the two substituents OH and Sk (side chain) mean that the respective substituent OH or Sk can be present both in α-position and β-position.

As alkyl groups $R^5$, $R^{5a}$, $R^6$, $R^7$, $R^8$ and $R^9$, straight-chain or branched-chain alkyl groups with 1–10 carbon atoms can be considered, such as, for example, methyl, ethyl, propyl, isopropyl, butyl, isobutyl, tert-butyl, pentyl, isopentyl, neopentyl, heptyl, hexyl, decyl as well as the appropriate unsaturated radicals (up to 3 double bonds), such as, for example, vinyl, propenyl, isopropenyl, butenyl, isobutenyl, butadienyl, hexenyl, etc.

Alkyl group $R^1$ is a straight-chain or branched-chain alkyl group with 1–3 carbon atoms, namely a methyl, ethyl, propyl or isopropyl group.

Alkyl groups $R^5$, $R^{5a}$, $R^6$, $R^7$, $R^8$ and $R^9$ can be substituted by 1–3 halogen atoms, hydroxy groups, $C_1$–$C_4$ alkoxy groups, $C_6$–$C_{12}$ aryl groups, which can be substituted by 1–3 halogen atoms, heteroaryl radicals, such as furyl, benzofuryl, thienyl, pyridyl, pyrazolyl, pyrimidinyl, oxazolyl, pyridazinyl, pyrazinyl, further di-($C_1$–$C_4$)-alkylamine and tri-($C_1$–$C_4$)-alkylammonium. Possible alkyl groups are those mentioned above; those alkyl groups that are not substituted or are singly substituted are preferred. As substituents, there can be mentioned, for example, halogens, such as fluorine, chlorine or bromine atoms, phenyl, dialkylamines, such as dimethylamino, diethylamino, $C_1$–$C_4$ alkoxy, such as methoxy, ethoxy. The $C_6$–$C_{12}$ aryl groups can also be substituted by the halogen atoms fluorine, chlorine or bromine.

As preferred alkyl group $R^1$, a methyl group can be cited, and as preferred alkyl groups $R^5$, $R^{5a}$, $R^6$, $R^7$, $R^8$ and $R^9$, those with 1–5 carbon atoms, such as, e.g., methyl, ethyl, propyl, isobutyl, butyl, tert-butyl can be mentioned.

Cycloalkyl groups $R^4$ can contain 3–10, preferably 3–6 carbon atoms in the ring. Ring $R^{4a}$ can be substituted by straight-chain or branched alkyl groups with 1–4 carbon atoms. For example, cyclopropyl, cyclobutyl, cyclopentyl, cyclohexyl, methylcyclopentyl, methylcyclohexyl can be mentioned.

Of side chains Sk that have the characteristic functional group $R^2$, all lead to good results, but in particular an esterified $\overline{\omega}$-hydroxyprop-1-enyl and but-1-enyl chain as well as an esterified 3-hydroxypropyl chain are to be emphasized.

For radical $R^2$, one of groups —O—($X^i_1$—$X^i_2$—$X^i_3$— ... —$X^i_p$), —C(=O)—($Y^i_1$—$Y^i_2$—$Y^i_3$— ... —$Y^i_p$) or —OC(=O)$R^3$ is preferred.

p preferably has the value 1, i.e., side chain Sk is then terminally esterified preferably with an amino acid or the carboxylic acid amide represents an amino acid.

The alkoxy groups that are contained in $R^{5a}$, $R^8$ or Z in general formula I are to contain 1 to 10 carbon atoms in each case, and methoxy, ethoxy, propoxy, isopropoxy and t-butyloxy groups are preferred.

In the $C_1$–$C_{10}$ acyl or $C_1$–$C_{10}$ acyloxy radical under definition Z, this is a $C_1$–$C_{10}$ alkanoyl(oxy) or benzoyl(oxy) radical, preferably a formyl, acetyl, propionyl or isopropionyl group.

Preferably one of the 17-substituents in the compounds according to this invention stands for a free hydroxy group, as is evident from general formula I. It is also possible within the scope of this invention, however, that this free hydroxy group is etherified with one of the radicals mentioned under the definition of alkyl groups R5, $R^{5a}$, $R^6$, $R^7$, $R^8$ and $R^9$ or is esterified with a $C_1$–$C_{10}$ acyl radical as mentioned under Z.

In the definitions for $R^6$, $R^7$ and Z, halogen means fluorine, chlorine, bromine or iodine.

If $R^8$ is a group Z, this is preferably a dialkylamino group —$NR^{9a}R^{9b}$, especially the dimethylamino group, a $C_1$–$C_{10}$ alkoxy group, especially the methoxy group or a $C_1$–$C_{10}$ acyl radical, in particular the formyl or acetyl radical.

As an aryl radical $R^8$ that is optionally substituted with a group Z, carbocyclic or heterocyclic aryl radicals, such as, e.g., phenyl, naphthyl, furyl, benzofuryl, thienyl, pyridyl, pyrazolyl, pyrimidinyl, oxazolyl, pyridazinyl, pyrazinyl, quinolyl, are suitable.

Preferred aryl radicals are phenyl, naphthyl, furyl, benzofuryl, thienyl, pyridyl; as substituted aryl radical $R^8$, first of all the 4-cyanophenyl radical and a 4-halophenyl radical, especially the 4-fluorophenyl radical, can be cited.

In compounds that are preferred according to the invention, substituents $R^6$ and $R^7$ respectively stand for a hydrogen atom.

A C—C single bond is preferably present between carbon atoms 6 and 7.

Amino acids HO—X—H or H—Y—OH can represent an α-, β- or γ-amino acid that is natural or unnatural, i.e., modified relative to their configuration or substitution.

Natural amino acids, such as, for example, glycine, alanine, valine, leucine, isoleucine, proline, are preferred.

A free amino group in HO—X—H or H—Y—OH can be provided with the protective groups that are familiar to one skilled in the art, such as, for example, tert-butyloxycarbonyl-(t-BOC), benzyloxycarbonyl, biphenyl-isopropyloxycarbonyl or 9-fluorenylmethoxycarbonyl.

The compounds below are especially preferred according to the invention:

(Z)-6'-(4-Cyanophenyl)-9,11α-dihydro-17β-hydroxy-17α-[3-(1-oxopropoxy)-1-propenyl]-4'H-naphtho[3',2',1':10,9,11]estr-4-en-3-one (Z)-6'-(4-cyanophenyl)-9,11α-dihydro-17β-hydroxy-17α-[3-[(1-oxopentyl)oxy]-1-propenyl]-4'H-naphtho[3',2',1':10,9,11]estr-4-en-3-one (Z)-6'-(4-cyanophenyl)-9,11α-dihydro-17β-hydroxy-17α-[3-[(1-oxoheptyl)oxy]-1-propenyl]-4'H-naphtho[3',2',1':10,9,11]estr-4-en-3-one (Z)-6'-(4-cyanophenyl)-9,11α-dihydro-17β-hydroxy-17α-[3-[(1-oxononyl)oxyl-1-propenyl]-4'H-naphtho[3',2',1':10,9,11]estr-4-en-3-one (Z)-6'-(4-cyanophenyl)-9,11α-dihydro-17β-hydroxy-17α-[3-[(1-oxododecyl)oxy]-1-propenyl]-4'H-naphtho[3',2',1':10,9,11]estr-4-en-3-one (Z)-6'-(4-cyanophenyl)-9,11α-dihydro-17β-hydroxy-17α-[3-(1-oxo-2-methylpropoxy)-1-propenyl]-4'H-naphtho[3',2',1':10,9,11]estr-4-en-3-one (Z)-6'-(4-cyanophenyl)-9,11α-dihydro-17α-[3-(3,3-dimethyl-1-oxobutoxy)-1-propenyl]-17β-hydroxy-4'H-naphtho[3',2',1':10,9,11]estr-4-en-3-one (Z)-6'-(4-cyanophenyl)-17α-[3-(3-cyclopentyl-1-oxopropoxy)-1-propenyl]-9,11α-dihydro-17β-hydroxy-4'H-naphtho[3',2',1':10,9,11]estr-4-en-3-one (Z)-6'-(4-cyanophenyl)-9,11α-dihydro-17α-[3-(1,4-dioxo-4-methoxybutoxy)-1-propenyl]-17β-hydroxy-4'H-naphtho[3',2',1':10,9,11]estr-4-en-3-one (Z)-6'-(4-cyanophenyl)-9,11α-dihydro-17α-[3-(1,4-dioxo-4-ethoxybutoxy)-1-propenyl]-17β-hydroxy-4'H-naphtho[3',2',1':10,9,11]estr-4-en-3-one (Z)-6'-(4-cyanophenyl)-9,11α-dihydro-17α-[3-(3-ethoxy-1-oxopropoxy)-1-propenyl]-17β-hydroxy-4'H-naphtho[3',2',1':10,9,11]estr-4-en-3-one (Z)-17α-[3-[(aminoacetyl)oxy]-1-propenyl]-6'-(4-cyanophenyl)-9,11α-dihydro-17β-hydroxy-4'H-naphtho[3',2',1':10,9,11]estr-4-en-3-one (Z)-6'-(4-cyanophenyl)-9,11α-dihydro-17α-[3-[[[[(1,1-dimethylethoxy),carbonyl]-amino] acetyl]oxy]-1-propenyl]-17β-hydroxy-4'H-naphtho[3',2',1':10,9,11]estr-4-en-3-one

[S-(Z)]-17α-[3-(2-amino-1-oxopropoxy)-1-propenyl]-6'-(4-cyanophenyl)-9,11α-dihydro-17β-hydroxy-4'H-naphtho[3',2',1':10,9,11]estr-4-en-3-one

[S-(Z)]-6'-(4-cyanophenyl)-9,11α-dihydro-17α-[3-[2-[[(1,1-dimethylethoxy)carbonyl]amino]-1- oxopropoxy]-1-propenyl]-17β-hydroxy-4'H-naphtho[3',2',1':10,9,11]estr-4-en-3-one

[S-(Z)]-17α-[3-(2-amino-3-methyl-1-oxobutoxy)-1-propenyl]-6'-(4-cyanophenyl)-9,11α-dihydro-17β-hydroxy-4'H-naphtho[3',2',1':10,9,11]estr-4-en-3-one

[S-(Z)]-6'-(4-cyanophenyl)-9,11α-dihydro-17α-[3-[2-[[(1,1-dimethylethoxy)carbonyl]amino]-3-methyl-1-oxobutoxy]-17β-hydroxy-4'H-naphtho[3',2',1':10,9,11]estr-4-en-3-one (Z)-9,11α-dihydro-17β-hydroxy-17α-[3-(1-oxopropoxy)-1-propenyl]-6'-(3-pyridinyl)-4'H-naphtho[3',2',1':10,9,11]estr-4-en-3-one (Z)-9,11α-dihydro-17β-hydroxy-17α-[3-[(1-oxopentyl)oxy]-1-propenyl]-6'-(3-pyridinyl)-4'H-naphtho[3',2',1':10,9,11]estr-4-en-3-one (Z)-9,11α-dihydro-17β-hydroxy-17α-[3-[(1-oxoheptyl)oxy]-1-propenyl]-6'-(3-pyridinyl)-4'H-naphtho[3',2',1':10,9,11]estr-4-en-3-one (Z)-9,11α-dihydro-17α-[3-(3,3-dimethyl-1-oxobutoxy)-1-propenyl]-6'-(3-pyridinyl)-17β-hydroxy-4'H-naphtho[3',2',1':10,9,11]estr-4-en-3-one (Z)-9,11α-dihydro-17α-[3-(1,4-dioxo-4-ethoxybutoxy)-1-propenyl]-17β-hydroxy-6'-(3-pyridinyl)-4'H-naphtho[3',2',1':10,9,11]estr-4-en-3-one

[S-(Z)]-17α-[3-(2-amino-1-oxopropoxy)-1-propenyl]-9,11α-dihydro-17β-hydroxy-6'-(3-pyridinyl)-4'H-naphtho[3',2',1':10,9,11]estr-4-en-3-one

[S-(Z)]-9,11α-dihydro-17α-[3-[2-[[(1,1-dimethylethoxy)carbonyl]amino]-1-oxopropoxy]-1-propenyl]-17β-hydroxy-6'-(3-pyridinyl)-4'H-naphtho[3',2',1':10,9,11]estr-4-en-3-one

[S-(Z)]-9,11α-dihydro-17α-[3-[2-[[(1,1-dimethylethoxy)carbonyl]amino]-3-methyl-1-oxobutoxy]-1-propenyl]-17β-hydroxy-6'-(3-pyridinyl)-4'H-naphtho[3',2',1':10,9,11]estr-4-en-3-one (S)-17β-[3-(2-amino-1-oxopropoxy)propyl]-11β-[4-(dimethylamino)phenyl]-17α-hydroxy-13α-estra-4,9-dien-3-one (S)-11β-[4-(dimethylamino)phenyl]-17β-[3-[2-[[(1,1-dimethylethoxy)carbonyl]amino]-1-oxopropoxy]propyl]-17α-hydroxy-13α-estra-4,9-dien-3-one (S)-17β-[3-(2-amino-3-methyl-1-oxobutoxy)propyl]-11β-[4-(dimethylamino)phenyl]-17α-hydroxy-13α-estra-4,9-dien-3-one (S)-11β-[4-(dimethylamino)phenyl]-17β-[3-[2-[[(1,1-dimethylethoxy)carbonyl]amino]-3-methyl-1-oxobutoxy]-1-propyl]-17α-hydroxy-13α-estra-4,9-dien-3-one

[S-(Z)]-17α-[3-(2-amino-1-oxopropoxy)-1-propenyl]-11β-[4-(dimethylamino)phenyl]-17β-hydroxyestr-4-en-3-one

[S-(Z)]-11β-[4-(dimethylamino)phenyl]-17α-[3-[2-[[(1,1-dimethylethoxy)carbonyl]amino]-1-oxopropoxy]-1-propenyl]-17β-hydroxyestr-4-en-3-one

[S-(Z)]-11β-[4-(dimethylamino)phenyl]-17α-[3-[2-[[(1,1-dimethylethoxy)carbonyl]amino]-3-methyl-1-oxobutoxy]-1-propenyl]-17β-hydroxyestr-4-en-3-one

[S-(Z)]-4'-[17α-[3-[2-[[(1,1-dimethylethoxy)carbonyl]amino]-1-oxopropoxy)-1-propenyl]-17β-hydroxy-3-oxoestr-4-en-11β-yl][1,1'-biphenyl]-4-carbonitrile

[S-(Z)]-4'-[17α-[3-[2-[[(1,1-dimethylethoxy)carbonyl]amino]-3-methyl-1-oxobutoxy]-1-propenyl]-17β-hydroxy-3-oxoestr-4-en-11β-yl][1,1'-biphenyl]-4-carbonitrile

[S-(Z)]-9,11α-dihydro-17α-[3-[[[(1,1-dimethylethoxy)carbonyl]amino]acetyloxy]-1-propenyl]-17β-hydroxy-6'-(3-pyridinyl)-4'H-naphtho[3',2',1':10,9,11]estr-4-en-3-one (S)-11β-[4-(dimethylamino)phenyl]-17β-[3-[[[(1,1-dimethylethoxy)carbonyl]amino]acetyloxy]propyl]-17α-hydroxy-13α-estra-4,9-dien-3-one

[S-(Z)]-11β-[4-(dimethylamino)phenyl]-17α-[3-[[[(1,1-dimethylethoxy)carbonyl]amino]acetyloxy]-1-propenyl]-17β-hydroxyestr-4-en-3-one

[S-(Z)]-4'-[17α-[3-[[[(1,1-dimethylethoxy)carbonyl]amino]acetyloxy]-1-propenyl]-17β-hydroxy-3-oxoestr-4-en-11β-yl][1,1'-biphenyl]-4-carbonitrile

[S-(Z)]-4'-[17α-[3-[2-amino-3-methyl-1-oxobutoxy]-1-propenyl]-17β-hydroxy-3-oxoestr-4-en-11β-yl][1,1'-biphenyl]-4-carbonitrile.

The invention further relates to a process for the production of steroid esters and amides of general formula I, in which a compound of general formula II

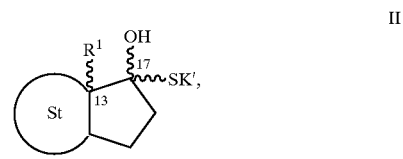

which has a terminal free hydroxyl group ($R^{2'}$=OH) in side chain Sk' and in which all other substituents have the meaning indicated in general formula I and functional groups that are present in St optionally can be protected according to the way known to one skilled in the art, with an amino acid HO—X—$R^5$, optionally protected ($R^5 \neq H$) on the amino group, or a peptide H—O—($X^i_1$—$X^i_2$—$X^i_3$— ... —$X^i_p$)—$R^5$ (p>1) or a carboxylic halide or anhydride ($R^3$—C(=O)Hal (Hal=Cl, Br) or [$R^3$—C(=O)—]$_2$O, optionally protected on the amino groups, being esterified, or, if $R^2$ in the compound of general formula I is to be a radical—C(=O)—($Y^i_3$—$Y^i_2$—$Y^i_3$— ... —$Y^i_p$)—$OR^5$, terminal hydroxy group $R^{2'}$first oxidizes completely to the carboxyl group, then the carboxylic acid obtained, optionally after activation, is reacted with an amino acid $R^5$—Y—$OR^{5'}$, optionally protected ($R^5 \neq H$) on the amino group, or a peptide $R^5$—($Y^i_1$—$Y^i_2$—$Y^i_3$— ... —$Y^i_p$)—$OR^5$ (p>1), optionally protected on the amino group, or an optionally protected amine HN$R^5$C(=O)$R^3$ is reacted to the appropriate amide and optionally protective groups that are present in St, the amino acid, the peptide or the amine are cleaved.

All reaction steps necessary for this synthesis method (protection of the functional groups in St, protection of the amino group, esterification reaction, oxidation of the hydroxyl group, acid activation by formation of a "reactive ester," amide formation, cleavage of the protective groups) are performed according to methods that are standard and familiar to one skilled in the art.

If p is to have a value>1 in the desired compound of general formula I, it can, instead of the peptide or amide, as described above, also be successively synthesized at the side chain by successive reaction steps on the side chain, for example,

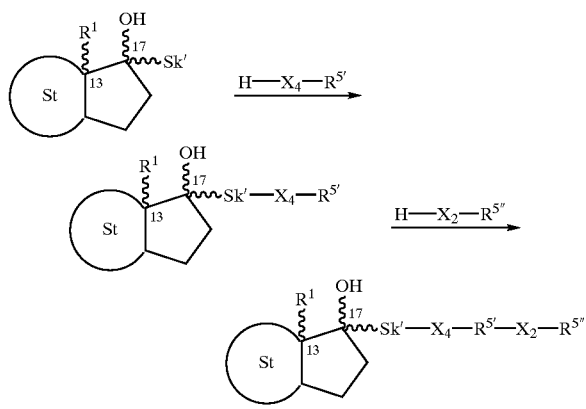

in which $R^{5'}$, $R^{5''}$ ... are the same or different and represent $R^5$ or H or an amino protective group and $X_1$, $X_2$, ... have the meaning indicated above under $X^i_{1 \ldots p}$.

The starting compounds of general formula II that are used for the production of compounds of general formula I with a free hydroxy group in the 17-side chain Sk' ($R^{2'}$=OH)—which are the compounds also designated elsewhere as "initial compounds"—as well as their production are described in a complete series of patents, patent applications and publications:

EP-A 0 129 499, EP-A 0259 248, EP-A 0 186 834, EP-A 0 447 014,

EP-A 0 116 974 EP-A 0 190 759, EP-A 0 147 361, EP-A 192 598, EP-A 0 283 428,

EP-A 0 404 283, WO-A 91/18917, WO-A 91/18918, WO-A 93/23020;

Steroids 44 (1984), 349 as well as other relevant bibliographic references known to one skilled in the art who is active in this field.

Many steroidal compounds, especially those with an lip-aryl radical, are partially very poorly soluble because of their substitution pattern, so that to preserve therapeutically relevant plasma levels, often superproportionally high single or multiple dosages or expensive formulation techniques must be used.

It has now been found, surprisingly enough, that the solubility of such compounds can be significantly improved if a free hydroxyl group is esterified or converted to an amide at a suitable point in the initial compound. In addition to improved solubility, the new compounds obtained therefore also possess increased biological action and selectivity compared to the corresponding initial compound.

Steroidal competitive progesterone antagonists, in which a free hydroxy group in the 17-side chain is esterified, are known already, for example, from the following European patent applications: a) 0 186 834, b) 0 283 428 and c) 0 404 283.

In case a), these are esters of the onapristone [11β-(4-dimethylaminophenyl)-17α-hydroxy-17β-(3-hydroxypropyl)-13α-methyl-4,9-gonadien-3-one], i.e., compounds with an ABC-ring system of partial formula B with alkyl radical $R^1$ in α-position and an esterified 17α-(3-hydroxypropyl) side chain. The chain length of the acyl radical is limited to a maximum of 10 carbon atoms.

In case b), the compounds with an ABC-ring system reflect partial formula C and in case c), the compounds with an ABC-ring system have partial formula A, i.a., a 17-alkyl, 17-alkenyl or 17-alkinyl side chain, which can have, terminally, an optionally esterified hydroxy function.

Nothing is said in these publications on an improvement of the solubility of the initial compounds with a terminal, free hydroxy group in the 17-side chain by esterification of this same hydroxy group.

Based on the improved solubility (Tab. 1) of the compounds according to the invention, it is possible in principle to reduce the dose required for a pharmacologically desired effect, which generally leads to a reduction of undesirable side effects and thus to an expanded therapeutic range.

They are therefore suitable for the production of such pharmaceutical agents which can lead, in the case of equal molar dosage of a compound of general formula I such as the appropriate initial compound in an appropriate formulation, to a higher bio-availability of the active ingredient, or in which the dose of a compound of general formula I can be reduced relative to the initial compound to achieve a comparable biological effect.

The new compounds of general formula I are thus valuable pharmaceutical active ingredients. They have a strong affinity to the gestagen receptor and have a surprisingly large area of antigestagenic, antiglucocorticoidal, antimineralcorticoidal and antiandrogenic properties. These important biological actions can be used for medicinal purposes.

Active ingredients of this type with pronounced antigestagenic activity are suitable for inducing abortions, since they displace from the receptor the progesterone that is required to maintain pregnancy. They are therefore valuable and advantageous with respect to their use for postcoital birth control. The compounds of general formula I according to the invention are also suitable for the production of preparations for contraception for the female (WO-A 93/23020).

They can be used, moreover, for hormonal irregularities, for inducing menstruation and for inducing labor. Other types of indications in the field of gynecology are the treatment of symptoms that accompany a dysmenorrhea as well as endometriosis.

Finally, they can be used for the treatment of hormone-dependent carcinomas.

TABLE 1

Solubility of a few steroid esters in comparison to the unesterified initial compounds. For solubility, the temperature is indicated in ° C., in which 50 mg of substance is dissolved in 1 ml of a 1:4 benzyl benzoate/castor oil mixture.

| Example | State | Solubility |
| --- | --- | --- |
| Ref. 1; Ex. 1 in DE 4216003 | crystalline | >>100 |
| 1 | crystalline | 100 → 23 |
| 2 | crystalline | 50 |
| 3 | foam | 23 |
| 4 | foam | 23 |
| 5 | foam | 23 |
| 6 | crystalline | 100 |
| 7 | foam | 23 |
| 8 | foam | 23 |
| 9 | crystalline | 50 |
| 10 | crystalline | 50 |
| 11 | crystalline | 100 |
| 12 | crystalline | 100 |
| 13 | foam | 50 |
| 14 | crystalline | 23 |
| 15 | foam | 23 |
| 16 | foam | 100 |
| 17 | foam | 50 |
| Ref. 2; Ex. 2 in DE 4216003 | crystalline | >>100 |
| 18 | crystalline | 50 |
| 19 | foam | 50 |

TABLE 1-continued

Solubility of a few steroid esters in comparison to the unesterified initial compounds. For solubility, the temperature is indicated in ° C., in which 50 mg of substance is dissolved in 1 ml of a 1:4 benzyl benzoate/castor oil mixture.

| Example | State | Solubility |
| --- | --- | --- |
| 20 | crystalline | 50 |
| 21 | crystalline | 50 |
| 22 | foam | 50 |
| 24 | foam | 50 |
| 25 | foam | 50 |
| 27 | foam | 23 |
| 29 | foam | 23 |
| 35 | foam | 23 |
| 36 | foam | 23 |
| Ref. 3; Ex. 16D in EP-A 0404283 | crystalline | >>100 |
| 30 | crystalline | 50 |
| 31 | foam | 23 |
| 32 | foam | 23 |
| 33 | foam | 50 |
| 34 | foam | 50 |
| 37 | foam | 23 |
| 38 | foam | 23 |
| 39 | foam | 50 |

The compounds of general formula I according to the invention also exhibit an antiglucocorticoidal activity and can thus also be used as pharmaceutical agents for treating corticoid-induced disorders (glaucoma) as well as for controlling side effects, which occur in the case of long-term treatment with glucocorticoids (Cushing's Syndrome). They therefore also make it possible to control the disorders that are attributable to a hypersecretion of glucocorticoids, particularly adiposity, arteriosclerosis, hypertension, osteoporosis, diabetes as well as insomnia.

The compounds of general formula I according to the invention with antiandrogenic activity can be used in the treatment of hypertrophy and carcinoma of the prostate. They further make possible a specific treatment of androgenization symptoms in females: the pathological hairiness in the case of hirsutism, the androgenetic alopecia as well as the increased oil gland function in the case of acne and seborrhea can be affected advantageously.

The invention thus also relates to pharmaceutical agents based on the compounds of general formula I that are pharmaceutically compatible, i.e, nontoxic in the doses used, together with the usual adjuvants and vehicles.

Finally, this invention also relates to the use of the compounds of general formula I for the production of pharmaceutical agents.

The compounds according to the invention can be processed into pharmaceutical preparations for enteral, percutaneous, parenteral or topical administration according to methods of galenicals known in the art. They can be administered in the form of tablets, coated tablets, gel capsules, granulates, suppositories, implants, injectable, sterile aqueous or oily solutions, suspensions or emulsions, ointments, creams and gels.

In this connection, the active ingredient or active ingredients can be mixed with the adjuvants that are usual in galenicals, such as, e.g., gum arabic, talc, starch, mannitol, methyl cellulose, lactose, surfactants such as Tween or Myrj, magnesium stearate, aqueous or nonaqueous vehicles, paraffin derivatives, wetting agents, dispersing agents, emulsifiers, preservatives and flavoring substances for taste correction (e.g., ethereal oils).

A dosage unit contains about 0.1–100 mg of active ingredient(s). The dosage of the compounds according to the invention in humans is approximately 0.1–1000 mg per day.

The following examples are used for a more detailed explanation of this invention:

EXAMPLE 1

(Z)-6'-(4-Cyanophenyl)-9,11α-dihydro-17β-hydroxy-17α-[3-(1-oxopropoxy)-1-propenyl]-4'H-naphtho[3',2',1':10,9,11]estr-4-en-3-one The solution of 400 mg (0.77 mmol) of (Z)-6'-(4-cyanophenyl)-9,11α-dihydro-17β-hydroxy-17α-(3-hydroxy-1-propenyl)-4'H-naphtho[3',2',1':10,9,11]estr-4-en-3-one in a mixture of 4 ml of anhydrous dichloromethane and 4 ml of anhydrous pyridine is mixed under an atmosphere of dry argon with 0.2 ml of propionic acid chloride and allowed to stir for 1 hour at 23° C. It is poured into saturated aqueous sodium bicarbonate solution, extracted several times with dichloromethane and the combined organic extracts are dried on sodium sulfate. After filtration and removal of solvent, the residue obtained is purified by chromatography on 200 ml of neutral aluminum oxide of activity stage III with a mobile solvent mixture of n-hexane and ethyl acetate. 346 mg (0.60 mmol, 78%) of the title compound is isolated as crystalline solid.

EXAMPLE 2

(Z)-6'-(4-Cyanophenyl)-9,11α-dihydro-17β-hydroxy-17α-[3-[(1-oxopentyl)oxy]-1-propenyl]-4'H-naphtho[3',2',1':10,9,11]estr-4-en-3-one Analogously to Example 1, 400 mg (0.77 mmol) of (Z)-6'-(4-cyanophenyl)-9,11α-dihydro-17β-hydroxy-17α-(3-hydroxy-1-propenyl)-4'H-naphtho[3',2',1':10,9,11]estr-4-en-3-one is reacted using pentanoic anhydride. After working-up and purification, 392 mg (0.65 mmol, 84%) of the title compound is isolated as crystalline solid.

EXAMPLE 3

(Z)-6'-(4-Cyanophenyl)-9,11α-dihydro-17β-hydroxy-17α-[3-[(1-oxoheptyl)oxy]-1-propenyl]-4'H-naphtho[3',2',1':10,9,11]estr-4-en-3-one Analogously to Example 1, 400 mg (0.77 mmol) of (Z)-6'-(4-cyanophenyl)-9,11α-dihydro-17β-hydroxy-17α-(3-hydroxy-1-propenyl)-4'H-naphtho[3',2',1':10,9,11]estr-4-en-3-one is reacted using heptanoic acid chloride. After working-up and purification, 345 mg (0.55 mmol, 71%) of the title compound is isolated as colorless foam.

EXAMPLE 4

(Z)-6'-(4-Cyanophenyl)-9,11α-dihydro-17β-hydroxy-17α-[3-[(1-oxononyl)oxy]-1-propenyl]-4'H-naphtho[3',2',1':10,9,11]estr-4-en-3-one Analogously to Example 1, 400 mg (0.77 mmol) of (Z)-6'-(4-cyanophenyl)-9,11α-dihydro-17β-hydroxy-17α-(3-hydroxy-1-propenyl)-4'H-naphtho[3',2',1':10,9,11]estr-4-en-3-one is reacted using nonanoic acid chloride. After working-up and purification, 373 mg (0.57 mmol, 73%) of the title compound is isolated as colorless foam.

EXAMPLE 5

(Z)-6'-(4-Cyanophenyl)-9,11α-dihydro-17α-hydroxy-17α-[3-[(1-oxododecyl)oxy]-1-propenyl]-4'H-naphtho[3',2',1':10,9,11]estr-4-en-3-one Analogously to Example 1, 400 mg (0.77 mmol) of (Z)-6'-(4-cyanophenyl)-9, 11α-dihydro-17β-hydroxy-17α-

(3-hydroxy-1-propenyl)-4'H-naphtho[3',2',1':10,9,11]estr-4-en-3-one is reacted using dodecanoic acid chloride. After working-up and purification, 411 mg (0.59 mmol, 76 k) of the title compound is isolated as colorless foam.

EXAMPLE 6

(Z)-6'-(4-Cyanophenyl)-9,11α-dihydro-17β-hydroxy-17α-[3-(1-oxo-2-methylpropoxy)-1-propenyl]-4'H-naphtho[3',2',1':10,9,11]estr-4-en-3-one Analogously to Example 1, 1 g (1.92 mmol) of (Z)-6'-(4-cyanophenyl)-9,11α-dihydro-17β-hydroxy-17α-(3-hydroxy-1-propenyl)-4'H-naphtho[3',2',1':10,9,11]estr-4-en-3-one is reacted using 2-methylpropanoic anhydride. After working-up and purification, 654 mg (1.11 mmol, 58%) of the title compound is isolated as crystalline solid.

EXAMPLE 7

(Z)-6'-(4-Cyanophenyl)-9,11α-dihydro-17α-[3-(3,3-dimethyl-1-oxobutoxy)-1-propenyl]-17β-hydroxy-4'H-naphtho[3',2',1':10,9,11]estr-4-en-3-one Analogously to Example 1, 400 mg (0.77 mmol) of (Z)-6'-(4-cyanophenyl)-9,11α-dihydro-17β-hydroxy-17α-(3-hydroxy-1-propenyl)-4'H-naphtho[3',2',1':10,9,11]estr-4-en-3-one is reacted using 3,3-dimethylbutanoic acid chloride. After working-up and purification, 340 mg (0.55 mmol, 71%) of the title compound is isolated as colorless foam.

EXAMPLE 8

(Z)-6'-(4-Cyanophenyl)-17α-[3-(3-cyclopentyl-1-oxopropoxy)-1-propenyl]-9,11α-dihydro-17β-hydroxy-4'H-naphtho[3',2',1':10,9,11]estr-4-en-3-one Analogously to Example 1, 400 mg (0.77 mmol) of (Z)-6'-(4-cyanophenyl)-9,11α-dihydro-17β-hydroxy-17α-(3-hydroxy-1-propenyl)-4'H-naphtho[3',2',1':10,9,11]estr-4-en-3-one is reacted using 3-cyclopentylpropionic acid chloride. After working-up and purification, 384 mg (0.60 mmol, 77%) of the title compound is isolated as colorless foam.

EXAMPLE 9

(Z)-6'-(4-Cyanophenyl)-9,11α-dihydro-17α-[3-(1,4-dioxo-4-methoxybutoxy)-1-propenyl]-17β-hydroxy-4'H-naphtho[3',2',1':10,9,11]estr-4-en-3-one Analogously to Example 1, 800 mg (1.54 mmol) of (Z)-6'-(4-cyanophenyl)-9,11α-dihydro-17β-hydroxy-17α-(3-hydroxy-1-propenyl)-4'H-naphtho[3', 2',1':10,9,11]estr-4-en-3-one is reacted using 4-methoxy-4-oxobutanoic acid chloride. After working-up and purification, 911 mg (1.44 mmol, 93%) of the title compound is isolated as crystalline solid.

EXAMPLE 10

(Z)-6'-(4-Cyanophenyl)-9,11α-dihydro-17α-[3-(1,4-dioxo-4-ethoxybutoxy)-1-propenyl]-17β-hydroxy-4'H-naphtho[3',2',1':10,9,11]estr-4-en-3-one Analogously to Example 1, 400 mg (0.77 mmol) of (Z)-6'-(4-cyanophenyl)-9,11α-dihydro-17β-hydroxy-17α-(3-hydroxy-1-propenyl)-4'H-naphtho[3',2',1':10,9,11]estr-4-en-3-one is reacted using 4-ethoxy-4-oxobutanoic acid chloride. After working-up and purification, 43;9 mg (0.68 mmol, 88%) of the title compound is isolated as crystalline solid.

EXAMPLE 11

(Z)-6'-(4-Cyanophenyl)-9,11α-dihydro-17α-[3-(3-ethoxy-1-oxopropoxy)-1-propenyl]-17βhydroxy-4'H-naphtho[3',2',1':10,9,11]estr-4-en-3-one Analogously to Example 1, 500 mg (0.96 mmol) of (Z)-6'-(4-cyanophenyl)-9,11α-dihydro-17β-hydroxy-17α-(3-hydroxy-1-propenyl)-4'H-naphtho[3',2',1':10,9,11]estr-4-en-3-one is reacted using 3-ethoxypropionic acid chloride. After working-up and purification, 387 mg (0.62 mmol, 65%) of the title compound is isolated as crystalline solid.

EXAMPLE 12

(Z)-17α-[3-[(Aminoacetyl)oxy]-1-propenyl]-6'-(4-cyanophenyl)-9,11α-dihydro-17β-hydroxy-4'H-naphtho[3',2',1':10,9,11]estr-4-en-3-one 780 mg (1.13 mmol) of the compound presented according to Example 13 is mixed at 0° C. under a dry atmosphere of argon with 5 ml of trifluoroacetic acid and allowed to stir for 20 minutes. It is poured into saturated aqueous sodium bicarbonate solution, extracted several times with dichloromethane and the combined organic extracts are dried on sodium sulfate. After filtration and removal of solvent, the residue obtained is purified by crystallization from ethyl acetate and 287 mg (0.49 mmol, 43%) of the title compound is isolated as crystalline solid.

EXAMPLE 13

(Z)-6'-(4-Cyanophenyl)-9,11α-dihydro-17α-[3-[[[[(1,1-dimethylethoxy)carbonyl]-amino]acetyl]oxy]-1-propenyl]-17βhydroxy-4'H-naphtho[3',2',1':10,9,11]estr-4-en-3-one The solution of 400 mg (0.77 mmol) of (Z)-6'-(4-cyanophenyl)-9,11α-dihydro-17β-hydroxy-17α-(3-hydroxy-1-propenyl)-4'H-naphtho[3',2',1':10,9,11]estr-4-en-3-one in a mixture of 4 ml of anhydrous dichloromethane and 4 ml of anhydrous pyridine is mixed under an atmosphere of dry argon with 200 mg of N-(tert-butoxycarbonyl)-glycine, 20 mg of 4-dimethylaminopyridine, 184 mg of dicyclohexylcarbodiimide and allowed to stir for 16 hours at 23° C. It is filtered off from precipitated urea, rewashed with a little dichloromethane and the residue that is obtained after removal of solvent is purified by chromatography on 200 ml of fine silica gel with a gradient system of n-hexane and ethyl acetate. 373 mg (0.55 mmol, 72%) of the title compound is isolated as colorless foam.

EXAMPLE 14

[S-(Z)]-17α-[3-(2-Amino-1-oxopropoxy)-1-propenyl]-6'-(4-cyanophenyl)-9,11α-dihydro-17β-hydroxy-4'H-naphtho [3',2',1':10,9,11]estr-4-en-3-one 760 mg (1.1 mmol) of the compound presented according to Example 15 is reacted analogously to Example 12 and after crystallization, 246 mg (0.42 mmol, 38%) of the title compound is isolated as crystalline solid.

EXAMPLE 15

(S-(Z)]-6'-(4-Cyanophenyl)-9,11α-dihydro-17α-[3-[2-[[(1,1-dimethylethoxy)carbonyl]amino]-1-oxopropoxy]-1-propenyl]-17β-hydroxy-4'H-naphtho[3',2',1':10,9,11]estr-4-en-3-one Analogously to Example 13, 1 g (1.91 mmol) of (Z)-6'-(4-cyanophenyl)-9,11α-dihydro-17β-hydroxy-17α-(3- hydroxy-1-propenyl)-4'H-naphtho[3',2',1':10,9,11]estr-4-en-3-one is reacted using N-(tert-butoxycarbonyl)-alanine. After working-up and purification, 1.27 g (1.84 mmol, 94%) of the title compound is isolated as colorless foam.

EXAMPLE 16

[S-(Z)]-17α-[3-(2-Amino-3-methyl-1-oxobutoxy)-1-propenyl]-6'-(4-cyanophenyl)-9,11α-dihydro-17β-hydroxy-4'H-naphtho[3',2',1':10,9,11]estr-4-en-3-one 800 mg (1.16 mmol) of the compound presented according to Example 17 is reacted analogously to Example 12 and 521 mg (0.84 mmol, 73%) of the title compound is isolated as colorless solid.

EXAMPLE 17

[S-(Z)]-6'-(4-Cyanophenyl)-9,11α-dihydro-17α-[3-[2-[[(1,1-dimethylethoxy)carbonyl]amino]-3-methyl-1-oxobutoxy]-17β-hydroxy-4'H-naphtho[3',2',1':10,9,11]estr-4-en-3-one Analogously to Example 13, 700 mg (1.35 mmol) of (Z)-6'-(4-cyanophenyl)-9,11α-dihydro-17β-hydroxy-17α-(3-hydroxy-1-propenyl)-4'H-naphtho[3',2',1':10,9,11]estr-4-en-3-one is reacted using N-(tert-butoxycarbonyl)-valine. After working-up and purification, 810 mg (1.13 mmol, 83%) of the title compound is isolated as colorless foam.

EXAMPLE 18

(Z)-9,11α-Dihydro-17β-hydroxy-17α-[3-(1-oxopropoxy)-1-propenyl]-6'-(3-pyridinyl)-4'H-naphtho[3',2',1':10,9,11]estr-4-en-3-one Analogously to Example 1, 500 mg (1.01 mmol) of (Z)-9,11α-dihydro-17β-hydroxy-17α-(3-hydroxy-1-propenyl)-6'-(3-pyridinyl)-4'H-naphtho[3',2',1':10,9,11]estr-4-en-3-one (for production, see DE 4216003) is reacted using propionic acid chloride. After working-up and purification, 261 mg (0.47 mmol, 47%) of the title compound is isolated as crystalline solid.

EXAMPLE 19

(Z)-9,11α-Dihydro-17β-hydroxy-17α-[3-[(1-oxopentyl)oxy]-1-propenyl]-6'-(3-pyridinyl)-4'H-naphtho[3',2',1':10,9,11]estr-4-en-3-one Analogously to Example 1, 500 mg (1.01 mmol) of (Z)-9,11α-dihydro-17β-hydroxy-17α-(3-hydroxy-1-propenyl)-6'-(3-pyridinyl)-4'H-naphtho[3',2',1':10,9,11]estr-4-en-3-one is reacted using pentanoic anhydride. After working-up and purification, 325 mg (0.56 mmol, 56%) of the title compound is isolated as colorless foam.

EXAMPLE 20

(Z)-9,11α-Dihydro-17βhydroxy-17α-[3-[(1-oxoheptyl)oxy]-1-propenyl]-6'-(3-pyridinyl)-4'H-naphtho[3',2',1':10,9,11]estr-4-en-3-one Analogously to Example 1, 500 mg (1.01 mmol) of (Z)-6'-(3-pyridinyl)-9,11α-dihydro-17β-hydroxy-17α-(3-hydroxy-1-propenyl)-4'H-naphtho[3',2',1':10,9,11]estr-4-en-3-one is reacted using heptanoic acid chloride. After working-up and purification, 255 mg (0.42 mmol, 42%) of the title compound is isolated as crystalline solid.

EXAMPLE 21

(Z)-9,11α-Dihydro-17α-[3-(3,3-dimethyl-1-oxobutoxy)-1-propenyl]-6'-(3-pyridinyl)-17βhydroxy-4'H-naphtho[3',2',1':10,9,11]estr-4-en-3-one Analogously to Example 1, 1 g (2.02 mmol) of (Z)-9,11α-dihydro-17β-hydroxy-17α-(3-hydroxy-1-propenyl)-6'-(3-pyridinyl)-4'H-naphtho[3',2',1':10,9,11]estr-4-en-3-one is reacted using 3,3-dimethylbutanoic acid chloride. After working-up and purification, 697 mg (1.20 mmol, 59%) of the title compound is isolated as crystalline solid.

EXAMPLE 22

(Z)-9,11α-Dihydro-17α-[3-(1,4-dioxo-4-ethoxybutoxy)-1-propenyl]-17β-hydroxy-6'-(3-pyridinyl)-4'H-naphtho[3',2',1':10,9,11]estr-4-en-3-one Analogously to Example 1, 500 mg (1.01 mmol) of (Z)-9,11α-dihydro-17β-hydroxy-17α-(3-hydroxy-1-propenyl)-6'-(3-pyridinyl)-4'H-naphtho[3',2',1':10,9,11]estr-4-en-3-one is reacted using 4-ethoxy-4-oxo-butanoic acid chloride. After working-up and purification, 265 mg (0.42 mmol, 42%) of the title compound is isolated as pale yellow foam.

EXAMPLE 23

[S-(Z)]-17α-[3-(2-Amino-1-oxopropoxy)-1-propenyl]-9,11α-dihydro-17β-hydroxy-6'-(3-pyridinyl)-4'H-naphtho[3',2',1':10,9,11]estr-4-en-3-one 770 mg (1.15 mmol) of the compound presented according to Example 24 is reacted analogously to Example 12 and after crystallization, 475 mg (0.84 mmol, 73%) of the title compound is isolated as solid.

EXAMPLE 24

[S-(Z)]-9,11α-Dihydro-17α-[3-[2-[[(1,1-dimethylethoxy)carbonyl]amino]-1-oxopropoxy]-1-propenyl]-17β-hydroxy-6'-(3-pyridinyl)-4'H-naphtho[3',2',1':10,9,11]estr-4-en-3-one Analogously to Example 13, 1 g (2.0 mmol) of (Z)-9,11α-dihydro-17β-hydroxy-17α-(3-hydroxy-1-propenyl)-6'-(3-pyridinyl)-4'H-naphtho[3',2',1':10,9,11]estr-4-en-3-one is reacted using N-(tert-butoxycarbonyl)-alanine. After working-up and purification, 995 mg (1.49 mmol, 75%) of the title compound is isolated as colorless foam.

EXAMPLE 25

[S-(Z)]-9,11α-Dihydro-17α-[3-[2-[[(1,1-dimethylethoxy)carbonyl]amino]-3-methyl-1-oxobutoxy]-1-propenyl]-17βhydroxy-6'-(3-pyridinyl)-4'H-naphtho[3',2',1':10,9,11]estr-4-en-3-one Analogously to Example 13, 496 mg (1.0 mmol) of (Z)-9,11α-dihydro-17β-hydroxy-17α-(3-hydroxy-1-propenyl)-6'-(3-pyridinyl)-4'H-naphtho[3',2',1':10,9,11]estr-4-en-3-one is reacted using N-(tert-butoxycarbonyl)-valine. After working-up and purification, 582 mg (838 μmol, 84%) of the title compound is isolated as colorless foam.

EXAMPLE 26

(S)-17β-[3-(2-Amino-1-oxopropoxy)propyl]-11β-[4-(dimethylamino)phenyl]-17α-hydroxy-13α-estra-4,9-dien-3-one 275 mg (0.44 mmol) of the compound presented according to Example 27 is mixed under an atmosphere of dry argon with 3.5 ml of a 4 M solution of hydrochloric acid in dioxane and stirred for 1 hour at 23° C. It is concentrated by evaporation in a vacuum and the residue obtained is optionally purified by chromatography on fine silica gel with a mixture of ethyl acetate, ethanol and triethylamine. 141 mg (0.27 mmol, 62%) of the title compound is isolated as yellow foam.

EXAMPLE 27

(S)-11β-[4-(Dimethylamino)phenyl]-17β-[3-[2-[[(1,1-dimethylethoxy)-carbonyl]amino]-1-oxopropoxy]propyl]-17α-hydroxy-13α-estra-4,9-dien-3-one Analogously to Example 13, 450 mg (1.0 mmol) of 11β-[4-(dimethylamino)phenyl]-17α-hydroxy-17β-(3-hydroxypropyl)-13α-estra-4,9-dien-3-one (for production, see DE 3468030) is reacted using N-(tert-butoxycarbonyl)-alanine. After working-up and purification, 475 mg (0.77 mmol, 77%) of the title compound is isolated as yellow foam.

EXAMPLE 28

(S)-17β-[3-(2-Amino-3-methyl-1-oxobutoxy)propyl]-11β-[4-(dimethylamino)phenyl]-17α-hydroxy-13α-estra-4,9-dien-3-one 418 mg (0.64 mmol) of the compound presented according to Example 29 is reacted analogously to Example 27, and 171 mg (0.31 mmol, 49%) of the title compound is isolated as pale yellow foam.

EXAMPLE 29

(S)-11β-[4-(Dimethylamino)phenyl]-17α-[3-[2-[[(1,1-dimethylethoxy)-carbonyl]amino]-3-methyl-1-oxobutoxy]-1-propyl]-17α-hydroxy-13α-estra-4,9-dien-3-one Analogously to Example 13, 450 mg (1.0 mmol) of 11β-[4-(dimethylamino)phenyl]-17α-hydroxy-17β-(3-hydroxypropyl)-13α-estra-4,9-dien-3-one is reacted using N-(tert-butoxycarbonyl)-valine. After working-up and purification, 539 mg (0.83 mmol, 830%) of the title compound is isolated as crystalline solid.

EXAMPLE 30

[S-(Z)]-17α-[3-(2-Amino-1-oxopropoxy)-1-propenyl]-11β-[4-(dimethylamino)phenyl]-17βhydroxyestr-4-en-3-one 100 mg (0.16 mmol) of the compound presented according to Example 31 is reacted analogously to Example 27 and, after crystallization from ethyl acetate, 71 mg (0.14 mmol, 85%) of the title compound is isolated as colorless solid.

EXAMPLE 31

[S-(Z)]-11β-[4-(Dimethylamino)phenyl]-17α-[3-[2-[[(1,1-dimethylethoxy)carbonyl]amino]-1-oxopropoxy]-1-propenyl]-17β-hydroxyestr-4-en-3-one Analogously to Example 13, 450 mg (1.0 mmol) of (Z)-11β-[4-(dimethylamino)phenyl]-17β-hydroxy-17α-(3-hydroxypropenyl)estr-4-en-3-one (for production, see EP-A 0404283) is reacted using N-(tert-butoxycarbonyl)-alanine. After working-up and purification, 428 mg (0.69 mmol, 69%) of the title compound is isolated as colorless foam.

EXAMPLE 32

[S-(Z)]-11β-[4-(Dimethylamino)phenyl]-17α-[3-[2-[[(1,1-dimethylethoxy)carbonyl]amino]-3-methyl-1-oxobutoxyl]-1-propenyl]-17β-hydroxyestr-4-en-3-one Analogously to Example 13, 450 mg (1.0 mmol) of (Z)-11β-[4-(dimethylamino)phenyl]-17β-hydroxy-17α-(3-hydroxy-1-propenyl)estr-4-en-3-one is reacted using N-(tert-butoxycarbonyl)-valine. After working-up and purification, 411 mg (0.63 mmol, 63%) of the title compound is isolated as colorless foam.

EXAMPLE 33

[S-(z)]-4'-[17α-[3-[2-[[(1,1-Dimethylethoxy)carbonyl]amino]-1-oxopropoxy]-1-propenyl]-17β-hydroxy-3-oxoestr-4-en-11β-yl][1,1'-biphenyl]-4-carbonitrile Analogously to Example 13, 550 mg (1.08 mmol) of (Z)-4'-[17α-(3-hydroxy-1-propenyl)-17β-hydroxy-3-oxoestr-4-en-11β-yl][1,1'-biphenyl-4-carbonitrile (for production, see EP-A 0404283) is reacted using N-(tert-butoxycarbonyl)-alanine. After working-up and purification, 652 mg (0.963mmol, 89%) of the title compound is isolated as colorless foam.

EXAMPLE 34

[S-(Z)]-4'-[17α-[3-[2-[[(1,1-Dimethylethoxy)carbonyl]amino]-3-methyl-1-oxobutoxy]-1-propenyl]-17β-hydroxy-3-oxoestr-4-en-11β-yl][1,1'-biphenyl]-4-carbonitrile Analogously to Example 13, 520 mg (1.02 mmol) of (Z)-4'-[17α-(3-hydroxy-1-propenyl)-17β-hydroxy-3-oxoestr-4-en-11β-yl][1,'-biphenyl]-4-carbonitrile is reacted using N-(tert-butoxycarbonyl)-valine. After working-up and purification, 612 mg (0.866 mmol, 85%) of the title compound is isolated as colorless foam.

EXAMPLE 35

[S-(Z)]-9,11α-Dihydro-17α-[3-[[[(1,1-dimethylethoxy)carbonyl]amino]acetyloxy]-1-propenyl]-17β-hydroxy-6'-(3-pyridinyl)-4'H-naphtho[3',2',1':10,9,11]estr-4-en-3-one Analogously to Example 13, 1 g (2.0 mmol) of (Z)-9,11α-dihydro-17β-hydroxy-17α-(3-hydroxy-1-propenyl)-6'-(3-pyridinyl)-4'H-naphtho[3',2',1':10,9,11]estr-4-en-3-one is reacted using N-(tert-butoxycarbonyl)-glycine. After working-up and purification, 574 mg (0.88 mmol, 44%) of the title compound is isolated as colorless foam.

EXAMPLE 36

(S)-11β-[4-(Dimethylamino)phenyl]-17β-[3-[[[(1,1-dimethylethoxy)carbonyl]amino]acetyloxy]propyl]-17α-hydroxy-13α-estra-4,9-dien-3-one Analogously to Example 13, 1 g (2.2 mmol) of 11β-[4-(dimethylamino)phenyl]-17α-hydroxy-17β-(3-hydroxypropyl)-13α-estra-4,9-dien-3-one (for production, see DE 3468030) is reacted using N-(tert-butoxycarbonyl)-glycine. After working-up and purification, 1.11 g (1.83 mmol, 84%) of the title compound is isolated as yellow foam.

EXAMPLE 37

[S-(Z)]-11β-[4-(Dimethylamino)phenyl]-17α-[3-[[[(1,1-dimethylethoxy)carbonyl]amino]acetyloxy]-1-propenyl]-17β-hydroxyestr-4-en-3-one Analogously to Example 13, 1 g (2.2 mmol) of (Z)-11β-[4-(dimethylamino)phenyl]-17β-hydroxy-17α-(3-hydroxypropenyl)estr-4-en-3-one (for production, see EP-A 0404283) is reacted using N-(tert-butoxycarbonyl)-glycine. After working-up and purification, 1.25 g (2.06 mmol, 94%) of the title compound is isolated as colorless foam.

EXAMPLE 38

[S-(Z)]-4'-[17α-[3-[[[(1,1-Dimethylethoxy)carbonyl]-amino]acetyloxy]-1-propenyl]-17β-hydroxy-3-oxoestr-4-en-11β-yl][1,1'-biphenyl]-4-carbonitrile Analogously to Example 13, 1.0 g (1.97 mmol) of (Z)-4'-[17α-(3-hydroxy-1-propenyl)-17β-hydroxy-3-oxoestr-4-en-11β-yl][1,1'-biphenyl]-4-carbonitrile (for production, see EP-A 0404283) is reacted using N-(tert-butoxycarbonyl)-glycine. After working-up and purification, 1.18 g (1.77 mmol, 90%) of the title compound is isolated as colorless foam.

EXAMPLE 39

[S-(Z)]-4'-[17α-[3-[2-Amino-3-methyl-1-oxobutoxy]-1-propenyl]-17β-hydroxy-3-oxoestr-4-en-11β-yl][1,1'-biphenyl]-4-carbonitrile Analogously to Example 26, 495 mg (0.70 mmol) of the compound presented according to Example 34 is reacted. After working-up and purification, 202 mg (0.333 mmol, 48%) of the title compound is isolated as pale yellow foam.

TABLE 2

Chemical shifting (δ = ppm) of selected signals of the compounds from the Examples in the $^1$H-NMR spectrum measured in $CDCl_3$.

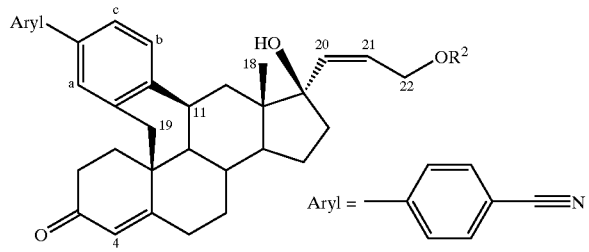

| Bsp. | H-4 | H-11 | H-18 | H-19 | H-20 | H-21 | H-22 | H-a | H-b | H-c | R² | OH |
|---|---|---|---|---|---|---|---|---|---|---|---|---|
| 1 | 5.90 | 3.37 | 0.50 | 3.32/2.81 | 5.72 | 5.56 | 5.16/4.89 | 7.32 | 7.56 | 7.43 | 1.17 (—CH₃), 2.39 (—COCH₂—) | 2.95 |
| 2 | 5.90 | 3.37 | 0.50 | 3.32/2.82 | 5.72 | 5.55 | 5.15/4.89 | 7.32 | 7.56 | 7.42 | 0.93 (—CH₃), 2.37 (—COCH₂—) | 3.00 |
| 3 | 5.90 | 3.37 | 0.50 | 3.32/2.81 | 5.72 | 5.55 | 5.14/4.89 | 7.31 | 7.56 | 7.43 | 0.89 (—CH₃), 2.35 (—COCH₂—) | 3.04 |
| 4 | 5.89 | 3.36 | 0.50 | 3.32/2.81 | 5.72 | 5.54 | 5.13/4.90 | 7.32 | 7.56 | 7.43 | 0.89 (—CH₃), 2.35 (—COCH₂—) | 3.02 |
| 5 | 5.90 | 3.36 | 0.50 | 3.32/2.81 | 5.72 | 5.54 | 5.14/4.90 | 7.32 | 7.56 | 7.42 | 0.88 (—CH₃), 2.35 (—COCH₂—) | 3.03 |
| 6 | 5.89 | 3.37 | 0.50 | 3.32/2.81 | 5.72 | 5.54 | 5.14/4.88 | 7.31 | 7.56 | 7.42 | 1.19 (—CH₃), 1.22 (—CH₃), | 3.07 |
| 7 | 5.90 | 3.37 | 0.50 | 3.32/2.81 | 5.73 | 5.55 | 5.13/4.89 | 7.31 | 7.56 | 7.42 | 1.06 (—C(CH₃)₃), 2.25 (—COCH₂—) | 3.20 |
| 8 | 5.89 | 3.36 | 0.50 | 3.31/2.81 | 5.72 | 5.54 | 5.14/4.90 | 7.32 | 7.56 | 7.42 | 2.37 (—COCH₂—) | 3.00 |
| 9 | 5.90 | 3.37 | 0.50 | 3.32/2.81 | 5.71 | 5.56 | 5.18/4.92 | 7.32 | 7.56 | 7.43 | 2.68 (—COCH₂—), 3.71 (—OCH₃) | 2.73 |
| 10 | 5.89 | 3.36 | 0.49 | 3.31/2.81 | 5.71 | 5.56 | 5.18/4.91 | 7.31 | 7.56 | 7.43 | 1.27 (—CH₃), 2.67 (—COCH₂—), 4.16 (—OCH₂—) | 2.72 |
| 11 | 5.89 | 3.35 | 0.49 | 3.31/2.81 | 5.72 | 5.56 | 5.18/4.91 | 7.31 | 7.56 | 7.42 | 1.20 (—CH₃), 2.62 (—COCH₂—), 3.52/3.72 (—OCH₂—) | 2.85 |
| 12 | 5.89 | 3.35 | 0.49 | 3.31/2.82 | 5.72 | 5.55 | 5.23/4.95 | 7.31 | 7.55 | 7.42 | 3.49 (—NCH₂—) | |
| 13 | 5.89 | 3.36 | 0.49 | 3.31/2.81 | 5.71 | 5.54 | 5.23/4.98 | 7.31 | 7.55 | 7.42 | 1.47 (—C(CH₃)₃), 3.96 (—NCH₂—), 5.03 (—NH) | |
| 14 | 5.90 | 3.36 | 0.49 | 3.31/2.81 | 5.72 | 5.53 | 5.21/4.92 | 7.31 | 7.55 | 7.42 | 1.49 (—CH₃), 3.60 (—NCH—), 4.04 (—NH) | |
| 15 | 5.90 | 3.36 | 0.49 | 3.31/2.81 | 5.72 | 5.53 | 5.21/4.92 | 7.31 | 7.56 | 7.42 | 1.41 (—CH₃), 1.46 (—C(CH₃)₃), 4.35 (—NCH—), 5.05 (—NH) | 2.66 |
| 16 | 5.89 | 3.35 | 0.50 | 3.30/2.80 | 5.72 | 5.53 | 5.23/4.92 | 7.31 | 7.56 | 7.42 | 0.93/1.00 (—CH₃) | |
| 17 | 5.89 | 3.36 | 0.49 | 3.31/2.81 | 5.72 | 5.54 | 5.23/4.96 | 7.31 | 7.56 | 7.42 | 0.91/0.99 (—CH₃), 1.45 (—C(CH₃)₃), 4.25 (—NCH—), 5.03 (—NH) | |

[Key:]
Bsp. = Example

TABLE 3

Chemical shifting (δ = ppm) of selected signals of the compounds from the Examples in the ¹H-NMR spectrum measured in CDCl₃.

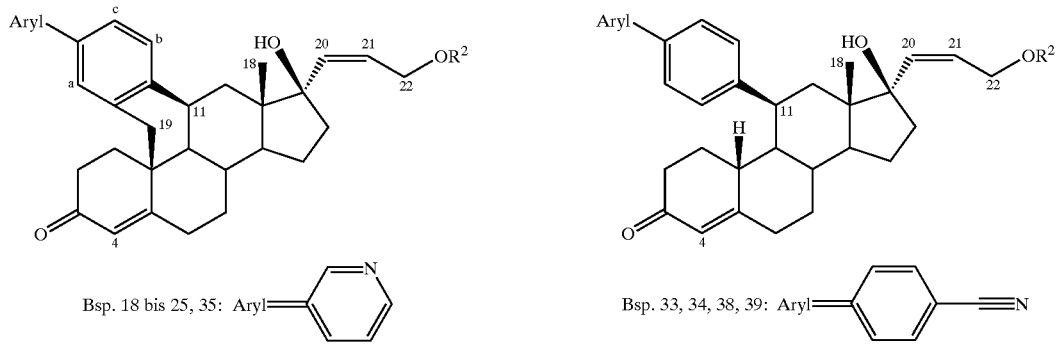

Bsp. 18 bis 25, 35: Aryl= (3-pyridyl)

Bsp. 33, 34, 38, 39: Aryl= (4-cyanophenyl)

| Bsp. | H-4 | H-11 | H-18 | H-19 | H-20 | H-21 | H-22 | H-a | H-b | H-c | R² | OH |
|---|---|---|---|---|---|---|---|---|---|---|---|---|
| 18 | 5.89 | 3.37 | 0.51 | 3.31/2.81 | 5.71 | 5.55 | 5.16/4.89 | 7.30 | 7.55 | 7.41 | 1.18 (—CH₃), 2.38 (—COCH₂—) | 2.93 |
| 19 | 5.90 | 3.37 | 0.51 | 3.31/2.81 | 5.71 | 5.54 | 5.14/4.89 | 7.30 | 7.56 | 7.41 | 0.94 (—CH₃), 2.35 (—COCH₂—) | 3.00 |
| 20 | 5.90 | 3.38 | 0.51 | 3.31/2.81 | 5.71 | 5.54 | 5.14/4.90 | 7.31 | 7.57 | 7.41 | 0.89 (—CH₃), 2.35 (—COCH₂—) | 3.02 |
| 21 | 5.90 | 3.38 | 0.51 | 3.32/2.82 | 5.72 | 5.55 | 5.13/4.90 | 7.30 | 7.56 | 7.41 | 1.07 (—C(CH₃)₃), 2.25 (—COCH₂—) | 3.19 |
| 22 | 5.89 | 3.37 | 0.50 | 3.32/2.82 | 5.71 | 5.55 | 5.19/4.92 | 7.30 | 7.56 | 7.41 | 1.27 (—CH₃), 2.67 (—COCH₂—) | |
| 24 | 5.90 | 3.37 | 0.50 | 3.32/2.82 | 5.71 | 5.54 | 5.21/4.98 | 7.30 | 7.57 | 7.41 | 1.41 (—CH₃), 1.45 (—C(CH₃)₃), 4.34 (—NCH—), 5.06 (—NH) | 2.66 |
| 25 | 5.89 | 3.37 | 0.50 | 3.31/2.82 | 5.72 | 5.54 | 5.22/4.97 | 7.30 | 7.55 | 7.41 | 0.92/0.99 (—CH₃), 1.46 (—C(CH₃)₃), 4.24 (—NCH—), 5.03 (—NH) | 2.79 |
| 33 | 5.88 | 3.42 | 0.72 | | 5.68 | 5.51 | 5.11/4.87 | | | | 1.40 (—CH₃), 1.46 (—C(CH₃)₃), 4.32 (—NCH—), 5.03 (—NH) | |
| 34 | 5.88 | 3.42 | 0.72 | | 5.69 | 5.51 | 5.13/4.86 | | | | 0.90/0.98 (—CH₃), 1.45 (—C(CH₃)₃), 4.23 (—NCH—), 5.02 (—NH) | |
| 35 | 5.90 | 3.37 | 0.50 | 3.32/2.83 | 5.72 | 5.54 | 5.23/5.00 | 7.31 | 7.56 | 7.41 | 1.47 (—C(CH₃)₃), 3.97 (—NCH₂—), 5.02 (—NH) | |
| 38 | 5.88 | 3.42 | 0.71 | | 5.69 | 5.52 | 5.13/4.89 | | | | 1.47 (—C(CH₃)₃), 3.93 (—NCH₂—), 5.01 (—NH) | |
| 39 | 5.88 | 3.42 | 0.73 | | 5.70 | 5.51 | 5.13/4.85 | | | | 0.91/0.99 (—CH₃), 3.31 (—NCH—) | |

[Key:]
Bsp. = Example
bis = to

TABLE 4

Chemical shifting (δ = ppm) of selected signals of the compounds from the Examples in the ¹H-NMR spectrum measured in CDCl₃.

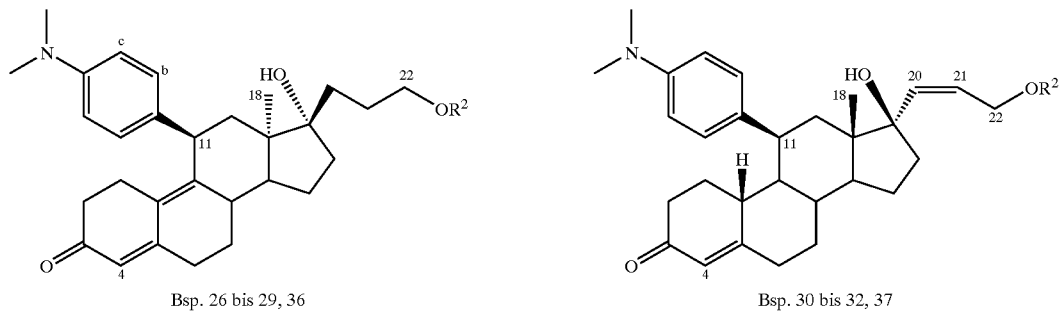

Bsp. 26 bis 29, 36

Bsp. 30 bis 32, 37

| Bsp. | H-4 | H-11 | H-18 | H-20 | H-21 | H-22 | H-b | H-c | R² | N—(CH₃)₂ |
|---|---|---|---|---|---|---|---|---|---|---|
| 26 | 5.69 | 3.76 | 1.07 | | | 4.11 | 7.00 | 6.65 | 1.32 (—CH₃), 3.52 (—NCH—), 5.22 (—NH) | 2.90 |
| 27 | 5.70 | 3.77 | 1.02 | | | 4.13 | 7.02 | 6.68 | 1.36 (—CH₃), 1.45 (—C(CH₃)₃), 4.29 (—NCH—), 5.03 (—NH) | 2.92 |
| 28 | 5.69 | 3.76 | 1.08 | | | 4.11 | 7.00 | 6.68 | 0.89/0.97 (—CH₃), 3.27 (—NCH—), 5.22 (—NH) | 2.91 |
| 29 | 5.70 | 3.78 | 1.02 | | | 4.15 | 7.01 | 6.68 | 0.87/0.95 (—CH₃), 1.45 (—C(CH₃)₃), 5.02 (—NH) | 2.93 |
| 31 | 5.84 | 3.28 | 0.72 | 5.67 | 5.48 | 5.10/4.86 | 7.25 | 6.66 | 1.39 (—CH₃), 1.45 (—C(CH₃)₃), 4.31 (—NCH—), 5.03 (—NH) | 2.93 |
| 32 | 5.83 | 3.28 | 0.72 | 5.67 | 5.48 | 5.11/4.86 | 7.25 | 6.67 | 0.90/0.97 (—CH₃), 1.46 (—C(CH₃)₃), 4.23 (—NCH—), 5.02 (—NH) | 2.94 |
| 36 | 5.70 | 3.77 | 1.02 | | | 4.15 | 7.03 | 6.68 | 1.44 (—C(CH₃)₃), 3.89 (—NCH₂—), 5.00 (—NH) | 2.93 |
| 37 | 5.84 | 3.28 | 0.72 | 5.67 | 5.49 | 5.12/4.89 | 7.25 | 6.67 | 1.45 (—C(CH₃)₃), 3.93 (—NCH₂—), 5.00 (—NH) | 2.93 |

[Key:]
Bsp. = Example
bis = to

EXAMPLE 40

[S-(Z)]-17α-[3-(2-Amino-1-oxopropoxy)-1-propenyl]-6'-(4-fluorophenyl)-9,11α-dihydro-17β-hydroxy-4'H-naphtho[3',2',1':10,9,11]estr-4-en-3-one Analogously to Example 26, 100 mg (0.15 mmol) of the compound presented according to Example 41 is reacted and, after working-up and purification, 62 mg (106 μmol, 71%) of the title compound is isolated as pale yellow foam.

$^1$H-NMR (CDCl$_3$); δ=0.50 (3H), 1.03–1.48 (4H), 1.37 (3H), 1.56–2.12 (11H), 2.26 (1H), 2.33–2.71 (4H), 2.79 (1H), 3.28 (1H), 3.33 (1H), 3.60 (1H), 4.93 (1H), 5.22 (1H), 5.53 (1H), 5.72 (1H), 5.89 (1H), 7.11 (2H), 7.25 (1H), 7.37 (1H), 7.43–7.62 (3H) ppm.

EXAMPLE 41

[S-(Z)]-6'-(4-Fluorophenyl)-9,11α-dihydro-17α-[3-[2-[[(1,1-dimethylethoxy)carbonyl]amino]-1-oxopropoxy]-1-propenyl]-17β-hydroxy-4'H-naphtho[3',2',1':10,9,11]estr-4-en-3-one Analogously to Example 13, 737 mg (1.44 mmol) of the compound presented according to Example 41a is reacted using N-(tert-butoxycarbonyl)-alanine and, after working-up and purification, 985 mg (1.44 mmol, 100%) of the title compound is isolated as colorless foam.

$^1$H-NMR (CDCl$_3$): δ=0.50 (3H), 1.03–1.39 (4H), 1.41 (3H), 1.46 (9H), 1.62–1.88 (5H), 1.96 (2H), 2.08 (1H), 2.28 (1H), 2.33–2.72 (5H), 2.80 (1H), 3.30 (1H), 3.33 (1H), 4.34 (1H), 4.97 (1H), 5.05 (1H), 5.22 (1H), 5.53 (1H), 5.72 (1H), 5.89 (1H), 7.12 (2H), 7.25 (1H), 7.37 (1H), 7.45–7.61 (3H) ppm.

EXAMPLE 41a (Z)-6'-(4-Fluorophenyl)-17α-(3-hydroxyprop-1-enyl)-9, 11α-dihydro-17β-hydroxy-4'-naphtho]3',2',1':10,9,11]estr-4-en-3-one The solution of 435 mg (8.52 μmol) of the compound in 5 ml of anhydrous tetrahydrofuran that is presented according to Example 41b is mixed with 43 mg of palladium/barium sulfate (10%), 0.44 ml of pyridine, and it is hydrogenated at one atmosphere until the calculated amount of hydrogen is taken up. The residue that is obtained after filtration and removal of solvent is purified by chromatography on fine silica gel using a gradient system of n-hexane, ethyl acetate and methanol. 318 mg (620 μmol, 73%) of the title compound is isolated as crystalline solid.

$^1$H-NMR (CDCl$_3$): δ=0.50 (3H), 1.16 (1H), 1.28–1.48 (3H), 1.59–1.91 (5H), 1.91–2.14 (3H), 2.27 (1H), 2.33–2.53 (2H), 2.55–2.72 (2H), 2.80 (1H), 2.91 (1H), 3.30 (1H), 3.34 (1H), 4.34 (2H), 5.68 (1H), 5.73 (1H), 5.89 (1H), 7.12 (2H), 7.25 (1H), 7.36 (1H), 7.43–7.61 (3H) ppm.

EXAMPLE 41b

6'-(4-Fluorophonyl)-17α-(3-hydroxyprop-1-inyl)-9, 11α-dihydro-17β-hydroxy-4'H-naphtho[3',2',1':10,9, 11]estr-4-on-3-one The solution of 3.4 g (4.86 mmol) of the compound in 170 ml of acetone that is presented according to Example 41c is mixed under one atmosphere of argon with 10 ml of a 4N hydrochloric acid, and it is heated for 2.5 hours to 50° C. It is poured into saturated sodium bicarbonate solution, extracted with dichloromethane and the combined organic extracts are dried on sodium sulfate. The residue that is obtained after filtration and removal of solvent is purified by chromatography on fine silica gel using a gradient system of n-hexane and ethyl acetate. 2.32 g (4.54 mmol, 93%) of the title compound is isolated as colorless foam.

$^1$H-NMR (CDCl$_3$): δ=0.45 (3H), 1.15–2.73 (19H), 2.81 (1H), 3.31 (1H), 3.40 (1H), 4.39 (2H), 5.90 (1H), 7.11 (2H), 7.26 (1H), 7.37 (1H), 7.49 (1H), 7.54 (2H) ppm.

EXAMPLE 41c

6'-(4-Fluorophonyl)-3-(3,3-dimethyltrimethylenedioxy)-17α-[3-(tetrahydropyran-2-yloxy)-prop-1-inyl]-9,11α-dihydro-4'H-naphtho[3',2',1':10,9,11]estran-5α,17β-diol The solution of 15.6 g (17.3 mmol) of 6'-(4-nonafluorobutylsulfonyloxy)-3-(3,3-dimethyltrimethylenedioxy)-17α-[3-(tetrahydropyran-2-yloxy)-prop-1-inyl]-9,11α-dihydro-4'H-naphtho[3',2',1':10,9,11]estr-4-en-5α,17β-diol, which was produced analogously to the process described in DE 4216003, is mixed in a mixture of 140 ml of toluene and 60 ml of ethanol under an atmosphere of argon with 0.4 ml of a 2M sodium carbonate solution, 1.45 g of lithium chloride, 2.62 g of 4-fluorobenzeneboronic acid, 988 mg of tetrakistriphenylphosphine palladium (O), and it is heated for 1 hour to 95° C. For completion of the reaction, the same amount of catalyst is added again and stirred for another 1.5 hours. The cooled mixture is diluted with ethyl acetate, washed with saturated sodium chloride solution and the organic phase is dried on sodium sulfate. The residue that is obtained after filtration and removal of solvent is purified by chromatography on fine silica gel using a gradient system of n-hexane and ethyl acetate. 10.2 g (14.6 mmol, 84%) of the title compound is isolated as colorless foam.

$^1$H-NMR (CDCl$_3$): δ=0.40 (3H), 0.93 (3H), 0.98 (3H), 1.22 (1H), 1.37–2.32 (24H), 2.56 (1H), 2.74 (1H), 3.18 (1H), 3.21 (1H), 3.44–3.68 (5H), 3.90 (1H), 4.37 (2H), 4.47 (1H), 4.88 (1H), 7.09 (2H), 7.22 (1H), 7.32 (1H), 7.45 (1H), 7.53 (2H) ppm.

EXAMPLE 42

(S)-6'-(4-Fluorophanyl)-9,11α-dihydro-17α-[3-[2-[[(1,1-dimethylethoxy)carbonyl]amino]-1-oxopropoxy]-1-propinyl]-17β-hydroxy-4'H-naphtho[3',2',1';10,9,11]estr-4-en-3-one Analogously to Example 13, 1.0 g (1.96 mmol) of the compound presented according to Example 41b is reacted using N-(tert-butoxycarbonyl)-alanine and, after working-up and purification, 1.18 g (1.73 mmol, 88%) of the title compound is isolated as colorless foam.

$^1$H-NMR (CDCl$_3$): δ=0.44 (3H), 1.12–2.73 (18H), 1.41 (3H), 1.45 (9H), 2.81 (1H), 3.30 (1H), 3.40 (1H), 4.36 (1H), 4.82 (2H), 5.02 (1H), 5.90 (1H), 7.12 (2H), 7.26 (1H), 7.37 (1H), 7.48 (1H), 7.53 (2H) ppm.

EXAMPLE 43

(S)-6'-(4-Fluorophanyl)-9,11α-dihydro-17α-[3-[2-[[(1,1-dimethylethoxy) carbonyl]amino]-1-oxopropoxy]-1-propyl]-17β-hydroxy-4'H-naphtho[3',2',1':10,9,11]estr-4-on-3-one Analogously to Example 13, 1.0 g (1.94 mmol) of the compound presented according to Example 43a is reacted using N-(tert-butoxycarbonyl)-alanine and, after working-up and purification, 1.10 g (1.60 mmol, 83%) of the title compound is isolated as colorless foam.

$^1$H-NMR (CDCl$_3$): δ=0.47 (3H), 1.08–2.72 (34H), 2.80 (1H), 3.31 (1H), 3.39 (1H), 4.11–4.39 (3H), 5.06 (1H), 5.89 (1H), 7.11 (2H), 7.25 (1H), 7.34 (1H), 7.48 (1H), 7.53 (2H) ppm. (1H), 7.54 (2H) ppm.

EXAMPLE 43a

6'-(4-Fluorophenyl)-17α-(3-hydroxypropyl)-9,11α-dihydro-17β-hydroxy-4'H-naphtho[3',2',1':10,9,11]estr-4-en-3-one Analogously to Example 41b, 603 mg (858 μmol) of the compound presented according to Example 43b is reacted and, after working-up and purification, 278 mg (540 μmol, 63%) of the title compound in isolated as colorless foam.

$^1$H-NMR (CDCl$_3$): δ=0.48 (3H), 1.03–1.41 (4H), 1.44–2.19 (14H), 2.27 (1H), 2.34–2.72 (4H), 2.80 (1H), 3.31 (1H), 3.38 (1H), 3.73 (2H), 5.89 (1H), 7.11 (2H), 7.25 (1H), 7.35 (1H), 7.48 (1H), 7.53 (2H) ppm.

EXAMPLE 43b

6'-(4-Fluorophenyl)-3-(3,3-dimethyltrimethylenedioxy)-17α-[3-(tetrahydropyran-2-yloxy)-propyl]-9,11α-dihydro-4'H-naphtho[3',2',1':10,9,11]estrane-5α,17β-diol The solution of 800 mg (1.14 mmol) of the compound in 30 ml of anhydrous ethanol that is presented according to Example 41c is mixed with 10 mg of palladium/carbon (10%), and it is hydrogenated at one atmosphere until the calculated amount of hydrogen is taken up. The residue that is obtained after filtration and removal of solvent is purified by chromatography on fine silica gel using n-hexane and ethyl acetate. 640 mg (910 μmol, 80%) of the title compound is isolated as colorless foam.

$^1$H-NMR (CDCl$_3$): δ=0.42 (3H), 0.94 (3H), 0.98 (3H), 1.20 (1H), 1.30–2.22 (28H), 2.46 (1H), 2.74 (1H), 3.17 (1H), 3.20 (1H), 3.40–3.68 (6H), 3.75–3.97 (2H), 4.45 (1H), 4.63 (1H), 7.10 (2H), 7.22 (1H), 7.31 (1H), 7.44 (1H), 7.53 (2H) ppm.

| Supplement to Table 1: | | |
| --- | --- | --- |
| Example | State | Solubility |
| Ref. 4; Ex. 41a | crystalline | 100 |
| 40 | crystalline | 50 |
| 41 | foam | 23 |
| Ref. 5; Ex. 41b | foam | 23 |
| 42 | foam | 23 |
| Ref. 6; Ex. 43a | foam | 23 |
| 43 | foam | 23 |

What is claimed is:

1. A steroid ester or amide of formula I

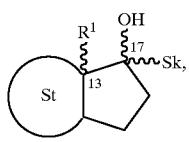

in which

R$^1$ is a C$_1$–C$_3$ alkyl radical in a α- or β-position,

SK is —C≡C—(CH$_2$)$_r$—R$^2$, (E) or (Z)—CH=CH—(CH$_2$)$_r$R$^2$R or —(CH$_2$)$_2$—(CH$_2$)$_r$—R$^2$, r is 1, 2 or 3,

R$^2$ is —O—(X$^i$)$_p$R$^5$, —C(=O)—(Y$^i$)$_p$—OR$^5$, —OC(=O)R$^3$, or —NHC(=O)R$^3$,

R$^3$ is —L—R$^4$,

L is an n-membered, straight- or branched-chain alkylene group, n, is an integer from 2 to 20, p is an integer from 1 to 6, R$^4$ is —(X$^i$)$_p$—R$^5$, or —C(=O)—(Y$^i$)$_p$—R$^5$, R$^5$ is hydrogen or a C$_1$–C$_{10}$ alkyl radical, (X$^1$)$_p$ is one or a series of C-terminally linked α-, β- or γ-amino acids, wherein the amino acids are the same or different, and wherein free amino groups optionally are protected by tert-butyloxycarbonyl, benzyloxycarbonyl, biphenylisopropyloxycarbonyl or 9-fluorenylmethoxycarbonyl, (Y$^1$)$_p$ is one or a series of N-terminally linked α-, β- or γ-amino acids, wherein the amino acids are the same or different, and wherein free amino groups optionally are protected by tert-butyloxycarbonyl, benzyloxycarbonyl, biphenylisopropyloxycarbonyl or 9-fluorenylmethoxycarbonyl, St is a steroidal ABC-ring system of partial formula C

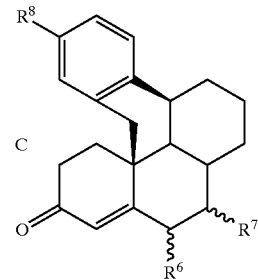

wherein optionally a double bond is present between carbon atoms 6 and 7 of St,

R$^6$ is hydrogen, C$_1$–C$_4$ alkyl, or halogen,

R$^7$ is hydrogen, C$_1$–C$_4$ alkyl, or halogen,

R$^8$ is a group Z or an aryl radical that is substituted by a group Z,

Z is hydrogen, halogen, —OH, —NO$_2$, —N$_3$, —CN, —NR$^{9a}$R$^{9b}$, —NHSO$_2$R$^9$, —CO$_2$R$^9$, C$_1$–C$_{10}$ alkyl, C$_1$–C$_{10}$ alkoxy, C$_1$–C$_{10}$ acloxy, or C$_1$–C$_{10}$ acyl, R$^{9a,b}$ are, each independently, hydrogen or C$_1$–C$_{10}$ alkyl, and R$^9$ is hydrogen or C$_1$–C$_{10}$ alkyl, or wherein R$^9$ is hydrogen, a physiologically compatible salt thereof with a base wherein Z is —CO$_2$H or an acid wherein Z is —NR$^{9a}$R$^{9b}$.

2. A compound according to claim 1, in which R$^1$ is a methyl group.

3. A compound according to claim 1, in which Sk is (E) or (Z)—CH=CH—(CH$_2$)$_r$—R$^2$ with r=1 or 2 or —(CH$_2$)$_2$—(CH$_2$)$_r$—R$^2$.

4. A compound according to claim 1, in which R$^2$ is —(X$^i$)$_p$—H, —C(=O)—(Y$^i$)$_p$—H, or —OC(=O)R$^3$.

5. A compound according to claim 1, in which p is 1.

6. A compound according to claim 1, wherein p is 1–6, and wherein (X$^i$)$_p$R$^5$ and (Y$^i$)$_p$ are, each independently, glycine, alanine, valine, leucine, isoleucine, or proline.

7. A compound according to claim 1, in which R$^8$ is —LR$^{9a}$R$^{9b}$, a C$_1$–C$_{10}$ alkoxy radical or a C$_1$–C$_{10}$ acyl radical.

8. A compound according to claim 1, in which $R^8$ is a dimethylamino group, a methoxy group, a formyl group or an acetyl radical.

9. A compound according to claim 1, in which $R^8$ is a phenyl, naphthyl, furyl, benzofuryl, thienyl, pyridyl, 4-cyanophenyl or 4-halophenyl radical.

10. A compound according to claim 1, in which $R^6$ and $R^7$ are hydrogen.

11. A compound according to claim 1, in which a single bond is present between carbon atoms 6 and 7.

12. A compound which is
(Z)-17α-[3-[(aminoacetyl)oxy]-1-propenyl]-6'-(4-cyanophenyl)-9,11α-dihydro -17β- hydroxy-4'H-naphtho [3',2',1':10,9,11]estr-4-en-3-one,
[S-(Z)]-17α-[3-(2-amino-1-oxopropoxy)-1-propenyl]-6'-(4-cyanophenyl)-9,11α-dihydro-17β-hydroxy-4'H-naphtho[3',2',1':10,9,11]estr-4-en-3-one,
[S-(Z)]-6'-(4-cyanophenyl)-9,11α-dihydro-17α-[3-[2-[[(1,1-dimethylethoxy)carbonyl]amino]-1-oxopropoxy]-1-propenyl]-17β-hydroxy-4'H-naphtho[3',2',1':10,9,11]estr-4-en-3-one,
[S-(Z)]-17α-[3-(2-amino-3-methyl-1-oxobutoxy)-1-propenyl]-6'-(4-cyanophenyl)-9,11α-dihydro-17β-hydroxy-4'H-naphtho[3',2',1':10,9,11]estr-4-en-3-one,
[S-(Z)]-6'-(4-cyanophenyl)-9,11α-dihydro-17α-[3-[2-[[(1,1-dimethylethoxy)carbonyl]amino]-3-methyl-1-oxobutoxy]-17β-hydroxy-4'H-naphtho[3',2'1':10,9,11] estr-4-en-3-one,
[S-(Z)]-17α-[3-(2-amino-1-oxopropoxy)-1-propenyl]9,11α-dihydro-17β-hydroxy-6'-(3-pyridinyl-4'H-naphtho[3',2',1':10,9,11]estr-4-en-3-one,
[S-(Z)]-9,11α-dihydro-17α-[3-[2-[[(1,1-dimethylethoxy)carbonyl]amino]-1-oxopropoxy]-1-propenyl]-17β-hydroxy-6'-(3-pyridinyl)-4'H-naphtho[3',2',1':10,9,11] estr-4-en-3-one,
[S-(Z)]-9,11α-dihydro-17α-[3-[2-[[(1,1-dimethylethoxy)carbonyl]amino]-3-methyl-1-oxobutoxy]-1-propenyl]-17β-hydroxy-6'-(3-pyridinyl)-4'H-naphtho[3',2',1':10,9,11]estr-4-en-3-one, or
[S-(Z)]-9,11α-dihydro-17α-[3-[[[(1,1-dimethylethoxy)carbonyl]amino]acetyloxy]-1-propenyl]-17β-hydroxy-6'-(3-pyridinyl)-4'-naphtho[3',2',1':10,9,11]estr-4-en-3-one.

13. A compound according to claim 6, wherein p is 1.

14. A compound which is
(Z)-6'-(4-cyanophenyl)-9,11α-dihydro-17β-hydroxy-17α-[3-[(1-oxopentyl)oxy]-1-propenyl]-4'H-naphtho[3',2',1':10,9,11]estr-4-en-3-one,
(Z)-6'-(4-cyanophenyl)-9,11α-dihydro-17β-hydroxy-17α-[3-[(1-oxoheptyl)oxy]-1-propenyl]-4'H-naphtho[3',2',1':10,9,11]estr-4-en-3-one,
(Z)-6'-(4-cyanophenyl)-9,11α-dihydro-17β-hydroxy-17α-[3-[(1-oxononyl)oxy]-1-propenyl]-4'H-naphtho[3',2',1':10,9,11]estr-4-en-3-one,
(Z)-6'-(4-cyanophenyl)-9,11α-dihydro-17β-hydroxy-17α-[3-[(1-oxononyl)oxy]-1-propenyl]-4'H-naphtho[3',2',1':10,9,11]estr-4-en-3-one,
(Z)-6'-(4-cyanophenyl)-9,11α-dihydro-17β-hydroxy-17α-[3-(1-oxo-2-methylpropoxy)-1-propenyl]-4'H-naphtho[3',2',1':10,9,11]estr-4-en-3-one,
(Z)-6'-(4-cyanophenyl)-9,11α-dihydro-17α-[3-(3,3-dimethyl-1-oxobutoxy)-1-propenyl]-17β-hydroxy-4'H-naphtho[3',2',1':10,9,11]estr-4-en-3-one,
(Z)-6'-(4-cyanophenyl)-17α-[3-(3-cyclopentyl-1-oxopropoxy)-1-propenyl]-9,11α-dihydro-17β-hydroxy-4'H-naphtho[3',2',1':10,9,11]estr-4-en-3-one,
(Z)-6'-(4-cyanophenyl)-9,11α-dihydro-17α-[3-(1,4-dioxo-4-methoxybutoxy)-1-propenyl]-17β-hydroxy-4'H-naphtho[3',2',1':10,9,11]estr-4-en-3-one,
(Z)-6'-(4-cyanophenyl)-9,11α-dihydro-17α-[3-(1,4-dioxo-4-ethoxybutoxy)-1-propenyl]-17β-hydroxy-4'-naphtho[3',2',1':10,9,11]estr-4-en-3-one,
(Z)-6'-(4-cyanophenyl)-9,11α-dihydro-17α-[3-(3-ethoxy-1-oxopropoxy)-1-propenyl]-17-hydroxy-4'H-naphtho[3',2',1':10,9,11]estr-4-en-3-one,
(Z)-9,11α-dihydro-17α-hydroxy-17α-[3-[(1-oxopentyl)oxy]-1-propenyl]-6'-(3-pyridinyl)-4'H-naphtho[3',2',1':10,9,11]estr-4-en-3-one,
(Z)-9,11α-dihydro-17β-hydroxy-17α-[3-[(1-oxoheptyl)oxy]-1-propenyl]-6'-(3-pyridinyl)-4'H-naphtho[3',2',1':10,9,11]estr-4-en-3-one,
(Z)-9,11α-dihydro-17α-[3-(3,3-dimethyl-1-oxobutoxy)-1-propenyl]-6'-(3-pyridinyl)-17β-hydroxy-4'H-naphtho[3',2',1':10,9,11]estr-4-en-3-one, or
(Z)-9,11α-dihydro-17α-[3-(1,4-dioxo-4-ethoxybutoxy)-1-propenyl]-17β-hydroxy-6'-(3-pyridinyl)-4'H-naphtho[3',2',1':10,9,11]estr-4-en-3-one.

15. (Z)-6'-(4-Cyanophenyl)-9,11α-dihydro-17α-[3-[[[(1,1-dimethylethoxy)carbonyl]-amino]acetyl]oxy]-1-propenyl]-17β-hydroxy-4'H-naphtho[3',2',1':10,9,11]estr-4-en-3-one.

16. A pharmaceutical composition comprising a compound of claim 1 and a pharmacologically acceptable carrier.

17. A pharmaceutical composition comprising a compound of claim 12 and a pharmacologically acceptable carrier.

18. A pharmaceutical composition comprising a compound of claim 14 and a pharmacologically acceptable carrier.

19. A method for achieving an antigestagenic, antiglucocorticoidal, antimineralcorticoidal or antiandrogenic effect, comprising administering a compound according to claim 1 to a host in need thereof.

20. A method of inducing abortion, achieving a contraceptive effect, treating hormonal irregularity, inducing menstruation, inducing labor, treating symptoms accompanying dysmenorrhea or endometriosis or treating hormone-dependent carcinoma, comprising administering an effective amount of a compound according to claim 1 to a host in need thereof.

21. A process for preparing a steroid ester or amide of formula I according to claim 1, comprising esterifying a compound of formula II

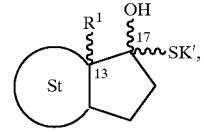

II which has a terminal free hydroxyl group $R^{2'}$ in side chain Sk' and in which all other groups are defined as in claim 1, or cleaving optional protective groups present in St, which is optionally protected with an amino acid HO—CX—$R^5$, or in embodiments wherein $R^5$ is not H, optionally protected on the amino group with an amino acid HO—CX—$R^5$, or is optionally protected on the amino groups with a peptide H—O—$(X')_p R^5$, wherein p is greater than 1, or a carboxylic halide Hal (O=)$CR^3$, wherein Hal is Cl or Br, or anhydride ($R^3$—C(=O)—)$_2$O, or in an embodiment wherein $R^2$ in the compound of formula I is —C(=O)—$(Y^i)_p$—$OR^5$, oxidizing the terminal hydroxyl group $R^{2'}$ to a carboxyl group and reacting the resultant carboxyl group with an amino acid $R^5$—Y—$OR^5$, or in an embodiment wherein $R^5$ is not H, cleaving optional protective groups present in St optionally protected on the amino group with an amino acid HO—CX—$R^5$, or is optionally protected on the amino groups with a peptide $R^5$—$(Y^i)_p$—$OR^5$, wherein p is greater than 1, or reacting an optionally protected amine $HNR^5C(=O)R^3$ to form an amide, and optionally cleaving the resultant amine.

* * * * *

UNITED STATES PATENT AND TRADEMARK OFFICE
CERTIFICATE OF CORRECTION

PATENT NO. : 6,596,713 B1  Page 1 of 1
DATED : July 22, 2003
INVENTOR(S) : Ulrich Klar et al.

It is certified that error appears in the above-identified patent and that said Letters Patent is hereby corrected as shown below:

Title page,
Item [75], Inventors, reads "(DE)" should read -- (DE); Kristof Chwalisz, Berlin (DE) --
Item [30], Foreign Application Priority Data, reads "44 43 488" should read -- 44 34 488 --

Column 24,
Line 7, reads "n, is" should read -- n is --
Line 12, reads "$(X^1)p$" should read -- $(X^i)p$ --
Line 19, reads "$(Y^1)p$" should read -- $(Y^i)p$ --
Line 47, reads "acloxy," should read -- acyloxy, --
Line 66, reads "--$LR^{9a}R^{9b}$" should read -- -$NR^{9a}R^{9b}$ --

Column 25,
Line 26, reads "3-methyl-1-" should read -- 3-methyl]-1- --
Line 29, reads "propenyl]9," should read -- propenyl]-9, --
Line 43, reads "4'-naphtho" should read -- 4'H-naphtho --
Line 57, reads "(1-oxononyl)" should read -- (1-oxododecyl) --

Column 26,
Line 5, reads "hydroxy-4'-" should read -- hydroxy-4'H- --
Lines 8 and 10, reads "-17-" should read -- -17β- --

Column 27,
Line 5, reads "$OR^5$" should read -- $OR^{5'}$ --

Signed and Sealed this

Fifth Day of October, 2004

JON W. DUDAS
*Director of the United States Patent and Trademark Office*